(12) United States Patent
Tirapu Azpiroz et al.

(10) Patent No.: US 11,709,819 B2
(45) Date of Patent: Jul. 25, 2023

(54) VALIDATING TEST RESULTS USING A BLOCKCHAIN NETWORK

(71) Applicant: International Business Machines Corporation, Armonk, NY (US)

(72) Inventors: Jaione Tirapu Azpiroz, Rio de Janeiro (BR); Ademir Ferreira da Silva, Sao Paulo (BR); Percival Silva de Lucena, Valinhos (BR); Matheus Esteves Ferreira, Rio de Janeiro (BR); Ricardo Luis Ohta, Sao Paulo (BR); Mathias B Steiner, Rio de Janeiro (BR)

(73) Assignee: International Business Machines Corporation, Armonk, NY (US)

( * ) Notice: Subject to any disclaimer, the term of this patent is extended or adjusted under 35 U.S.C. 154(b) by 279 days.

(21) Appl. No.: 17/039,719

(22) Filed: Sep. 30, 2020

(65) Prior Publication Data

US 2022/0100731 A1    Mar. 31, 2022

(51) Int. Cl.
G06F 16/23   (2019.01)
G06N 20/00   (2019.01)
(Continued)

(52) U.S. Cl.
CPC ......... *G06F 16/2365* (2019.01); *G01N 33/02* (2013.01); *G06N 5/04* (2013.01);
(Continued)

(58) Field of Classification Search
CPC ...... G06F 16/2365; G01N 33/02; G06N 5/04; G06N 20/00; G06N 3/08; G06N 5/022;
(Continued)

(56) References Cited

U.S. PATENT DOCUMENTS 8,160,758 B2   4/2012   Call et al.
8,972,357 B2   3/2015   Shim et al.
(Continued)

FOREIGN PATENT DOCUMENTS

AU    2016351569 B2    5/2017
CA       2392962 A1   10/2002
(Continued)

OTHER PUBLICATIONS

Balagurusamy et al., "Crypto anchors," IBM, vol. 63, No. 2/3, Paper 4, Mar./May 2019, 12 pages Authorized licensed use limited to: IBM. Downloaded on Jul. 7, 2020 at 16:33:11 UTC from IEEE Xplore.

(Continued)

*Primary Examiner* — Walter L Lindsay, Jr.
*Assistant Examiner* — Geoffrey T Evans
(74) *Attorney, Agent, or Firm* — Grant Johnson

(57) ABSTRACT

A validation method applied to sensor data prior to submitting to a blockchain, a computer program product, and a system for validating chemical data. One embodiment may comprise receiving a sensor captured result at an application, applying the sensor captured result to a domain-specific statistical model of expected range of variability of measured results to extract a distribution of expected sensor values, computing a confidence value in the sensor captured result using the domain-specific statistical model, validating the confidence value against a required threshold of confidence, and submitting the sensor captured result for appending to the blockchain if the confidence level is validated against the threshold of confidence.

20 Claims, 22 Drawing Sheets

(51) Int. Cl.
  *G01N 33/02* (2006.01)
  *G06N 5/04* (2023.01)
  *H04L 9/00* (2022.01)
  *H04L 9/32* (2006.01)
  *H04W 4/029* (2018.01)
(52) U.S. Cl.
  CPC .......... *G06N 20/00* (2019.01); *H04L 9/3247* (2013.01); *H04L 9/50* (2022.05); *H04W 4/029* (2018.02)
(58) Field of Classification Search
  CPC ....... G06N 3/0427; H04L 9/3247; H04L 9/50; H04W 4/029; H04W 4/021
  See application file for complete search history.

(56) References Cited

U.S. PATENT DOCUMENTS

| | | |
|---|---|---|
| 9,213,079 B2 | 12/2015 | Kenington et al. |
| 10,250,381 B1 | 4/2019 | Rice |
| 10,340,038 B2 | 7/2019 | Witchey |
| 10,452,031 B2 | 10/2019 | Witter |
| 2004/0039489 A1 | 2/2004 | Moore et al. |
| 2006/0282467 A1 | 12/2006 | Peterson et al. |
| 2007/0174900 A1 | 7/2007 | Marueli et al. |
| 2013/0210450 A1 | 8/2013 | Kenington et al. |
| 2013/0225202 A1 | 8/2013 | Shim et al. |
| 2015/0247190 A1 | 9/2015 | Ismagilov et al. |
| 2016/0179994 A1 | 6/2016 | Levine et al. |
| 2017/0005804 A1 | 1/2017 | Zinder |
| 2017/0102466 A1 | 4/2017 | Petkus et al. |
| 2017/0134280 A1 | 5/2017 | Davis |
| 2017/0154438 A1 | 6/2017 | Kisner et al. |
| 2017/0247743 A1 | 8/2017 | Leung et al. |
| 2018/0096347 A1 | 4/2018 | Goeringer et al. |
| 2018/0189312 A1 | 7/2018 | Alas et al. |
| 2018/0240134 A1 | 8/2018 | Camenisch et al. |
| 2018/0322590 A1 | 11/2018 | Sundararajan et al. |
| 2018/0349520 A1 | 12/2018 | Bhalla et al. |
| 2018/0368819 A1 | 12/2018 | Gogineni |
| 2018/0375668 A1 | 12/2018 | Diehl et al. |
| 2019/0057171 A1 | 2/2019 | Qin et al. |
| 2019/0065685 A1 | 2/2019 | Pickover et al. |
| 2019/0073645 A1 | 3/2019 | Dazin |
| 2019/0130368 A1 | 5/2019 | Li et al. |
| 2019/0188712 A1 | 6/2019 | Fedorov et al. |
| 2019/0190698 A1 | 6/2019 | Nuzzi |
| 2019/0195852 A1 | 6/2019 | Bryant, Jr. et al. |
| 2020/0143300 A1 | 5/2020 | Weldemariam et al. |

FOREIGN PATENT DOCUMENTS

| | | |
|---|---|---|
| CN | 101673450 A | 3/2010 |
| CN | 201897593 U | 7/2011 |
| CN | 105848465 A | 8/2016 |
| CN | 106405660 A | 2/2017 |
| CN | 106406403 A | 2/2017 |
| CN | 108169161 A | 6/2018 |
| CN | 108370802 A | 8/2018 |
| CN | 108564515 A | 9/2018 |
| CN | 108803755 A | 11/2018 |
| CN | 108828992 A | 11/2018 |
| CN | 109115268 A | 1/2019 |
| CN | 109355177 A | 2/2019 |
| CN | 109358177 A | 2/2019 |
| CN | 109392676 A | 3/2019 |
| CN | 109612445 A | 4/2019 |
| CN | 109634248 A | 4/2019 |
| EP | 2473956 A1 | 7/2012 |
| EP | 3155372 A1 | 4/2017 |
| EP | 3203444 A1 | 8/2017 |
| EP | 3471006 A1 | 4/2019 |
| EP | 3975077 A1 * | 3/2022 |
| ES | 2649184 T3 | 1/2018 |
| JP | 2017023021 A | 2/2017 |
| KR | 101057470 B1 | 8/2011 |
| KR | 1020140026935 A | 3/2014 |
| KR | 101824653 B1 | 2/2018 |
| RU | 129656 U1 | 6/2013 |
| WO | 2004027677 A1 | 4/2004 |
| WO | 2010131197 A2 | 11/2010 |
| WO | 2014076254 A1 | 5/2014 |
| WO | 2016109809 A1 | 7/2016 |
| WO | 2016183473 A1 | 11/2016 |
| WO | WO-2017039473 A1 * | 3/2017 |
| WO | 2017083143 A1 | 5/2017 |
| WO | 2017180382 A1 | 10/2017 |
| WO | 2018069566 A1 | 4/2018 |
| WO | 2018099920 A1 | 6/2018 |
| WO | 2018125887 A2 | 7/2018 |
| WO | 2018215874 A1 | 11/2018 |
| WO | 2018232221 A1 | 12/2018 |
| WO | 2019021313 A1 | 1/2019 |
| WO | 2019043536 A1 | 3/2019 |
| WO | 2019043537 A1 | 3/2019 |
| WO | 2019090264 A1 | 5/2019 |
| WO | 2019090313 A1 | 5/2019 |
| WO | 2019133568 A1 | 7/2019 |

OTHER PUBLICATIONS

Gökçe et al., "High-Content Optical Codes for Protecting Rapid Diagnostic Tests from Counterfeiting," ACS Publications, Analytical Chemistry, 2018, 8 pages, https://pubs.acs.org/doi/10.1021/acs.analchem.8b00826.

Steiner, "Enveritas Pilots IBM's AI-powered AgroPad to Help Coffee Farmers," IBM Research Blog, Dec. 9, 2019, 9 pages, https://www.ibm.com/blogs/research/2019/12/enveritas-pilots-ibms-ai-powered-agropad-to-help-coffee-farmers/#:~:text=A%20smart%2C%20AI-powered%20paper%20device%20the%20size%20of,smallholder%20coffee%20farmers%20save%20money%20and%20improve%20sustainability.

Ohto et al., "Mobile Chemical Analysis," IBM U.S. Appl. No. 15/941,692, filed Mar. 30, 2018.

"Drones, Sensors and Blockchain for water quality control in the Volga river to promote trustworthy data and transparency," Libelium,, Nov. 28, 2018, 11 pages, http://www.libelium.com/drones-sensors-and-blockchain-for-water-quality-control-in-the-volga-river-to-promote-trustworthy-data-and-transparency/.

"Data validation and reconciliation," Wikipedia, Printed Sep. 25, 2020, 10 pages https://en.wikipedia.org/wiki/Data_validation_and_reconciliation.

Xiong et al. "Blockchain Technology for Agriculture: Applications and Rationale," Frontiers in Blockchain, Feb. 21, 2020, 7 pages, doi: 10.3389/fbloc.2020.00007.

Bore et al., "ADW: Blockchain-enabled Small-scale Farm Digitization," arXiv:2003.06862, Mar. 15, 2020, 9 pages.

Salah et al., "Blockchain-Based Soybean Traceability in Agricultural Supply Chain," IEEE Access, May 20, 2019, 11 pages, Digital Object Identifier 10.1109/ACCESS.2019.2918000.

Ge et al., "Blockchain for Agriculture and Food," Findings from the pilot study, Wageningen Economic Research, Dec. 2017, 40 pages.

Lin et al., "Blockchain: The Evolutionary Next Step for ICT E-Agriculture," MDPI Environments, Jul. 8, 2017, 13 pagse, https://www.mdpi.com/2076-3298/4/3/50/pdf.

Mell et al., "The NIST Definition of Cloud Computing," Recommendations of the National Institute of Standards and Technology, U.S. Department of Commerce, Special Publication 800-145, Sep. 2011, 7 pages.

Anonymous, "Precision Farming Market Size Worth $12.9 Billion By 2027", Grandview Research, Feb. 2020, 5 pages, <https://web.archive.org/web/20201031142935/https://www.grandviewresearch.com/press-release/global-precision-farming-market>.

Anonymous, "Sustainable agriculture", PRI, Aug. 19, 2018, 4 pages, <https://www.unpri.org/thematic-and-impact-investing/impact-investing-market-map-sustainable-agriculture/3542.article>.

\* cited by examiner

VALIDATING TEST RESULTS USING A BLOCKCHAIN NETWORK

BACKGROUND

The present disclosure relates to validating test results, and more specifically, to validating test results using a blockchain network.

The development of the EDVAC system in 1948 is often cited as the beginning of the computer era. Since that time, computer systems have evolved into extremely complicated devices. Today's computer systems typically include a combination of sophisticated hardware and software components, application programs, operating systems, processors, buses, memory, input/output devices, and so on. As advances in semiconductor processing and computer architecture push performance higher and higher, even more advanced computer software has evolved to take advantage of the higher performance of those capabilities, resulting in computer systems today that are much more powerful than just a few years ago.

One application of these new capabilities is blockchain technology. The blockchain generally refers to a shared, immutable ledger that facilitates the process of recording transactions and tracking assets in a business network. An asset can be tangible (a house, a car, cash, land) or intangible (intellectual property, patents, copyrights, branding). Virtually anything of value can be tracked and traded on a blockchain network, which may reduce risk, verify and trace origin, and cut costs for all involved.

SUMMARY

According to embodiments of the present disclosure, a method for validating sensor captured results, using blockchain records via a cloud application, which may apply domain-specific validation methods that require geographical and geolocation-dependent information such as, but not limited to, farming applications. The method may use historical measurement records, historical weather conditions records and domain-specific data, from current and neighboring measuring sites to predict the likely progression of prior measurement records and to compare to the new measurement to compute a confidence score.

According to embodiments of the present disclosure, a method may perform a measurement with a Universal Unique ID enabled device, digitize the measured data, and determine a geospatial position of the measurement by the sensing device. Then, embodiments may submit the sensor captured results with sample geolocation and sensor identification to a blockchain cloud application, where the results and the non-overlapping tile identification of the target measurement location are identified. The cloud application may then associate the sensor measurement site with the non-overlapping tile identification, retrieve historical measurements of current tile and neighboring tiles together with geographical and geolocation-dependent domain-specific (e.g., farming) data and historical weather data from knowledge database. The method may then apply the data to a domain-specific statistical model of an expected range of variability of measured results to extract the distribution of expected sensor measurements. Finally, some embodiments compute the measurement confidence against the expected range and validates the measurement confidence level against a required threshold of confidence and appends the sensor measurement to the blockchain thread for that location.

According to embodiments of the present disclosure, a system comprising a sensing service that performs analysis on the field and possesses a Universal Unique ID (UUID); a data digitalization device, which may include a mobile device application installed on a mobile device equipped with a camera for enabling sensor data capturing, UUID capturing and processing and for providing geolocation and communication; and a blockchain cloud application to validate and store sensing device data, which may include a transaction data composer, a chaincode interface module, and a distributed ledger.

According to embodiments of the present disclosure, a validation method applied to sensor data prior to submitting to a blockchain comprising receiving a sensor captured result at an application, applying the sensor captured result to a domain-specific statistical model of expected range of variability of measured results to extract a distribution of expected sensor values, computing a confidence value in the sensor captured result using the domain-specific statistical model, validating the confidence value against a required threshold of confidence, and submitting the sensor captured result for appending to the blockchain if the confidence level is validated against the threshold of confidence.

According to embodiments of the present disclosure, computer program product for validating sensor data prior to submitting to a blockchain. The computer program product may comprise a computer readable storage medium having program instructions embodied therewith. The program instructions may be executable by a processor to cause the processor to receive a sensor captured result at an application, apply the sensor captured result to a domain-specific statistical model of expected range of variability of measured results to extract a distribution of expected sensor values, compute a confidence value in the sensor captured result using the domain-specific statistical model, validate the confidence value against a required threshold of confidence, and submit the sensor captured result for appending to the blockchain if the confidence level is validated against the threshold of confidence.

According to embodiments of the present disclosure, a verification and validation method applied to geography-dependent sensor data prior to submitting to a blockchain comprising receiving sensor captured results with sample geolocation and unique sensor identification at an application, validating a sensor using the unique sensor identification, identifying a non-overlapping tile identification of the sensor captured results, associating the sensor captured results with the non-overlapping tile identification, retrieving historical and neighboring tiles' records corresponding to the non-overlapping tile identification, retrieving geographical and domain specific data from a knowledge database, training a domain-specific statistical model of an expected range of variability using the historical and neighboring tiles' records and the geographical and domain specific data, applying the sensor captured results to the domain-specific statistical model of the expected range of variability to extract a distribution of expected sensor values, calculate a distribution of expected sensor values, applying the sensor captured result, computing a measurement confidence in the sensor captured results using the calculated distribution of expected sensor values and the trained domain-specific statistical model, validate the measurement confidence against a required threshold of confidence, and in response to a successful validation, appending the sensor measurement to a blockchain thread for that geolocation. The validating, identifying, and retrieving may be done by the application in some embodiments.

According to embodiments of the present disclosure, a blockchain network comprising a blockchain application including an intermediate verification layer. The intermediate verification layer may comprise a geolocation module that identifies a non-overlapping geographical tile reference for a measurement, a data retrieval module to retrieve historical data for the non-overlapping geographical tile reference, a validation module that receives the retrieved data, calculates a predicted value for the sensor captured results, and calculates a confidence score based on a comparison between the predicted value and the measurement, and a blockchain transaction data composer that appends the measurement to a distributed ledger based on the confidence score. In some embodiments, the intermediate verification layer may comprise a smart contract. In some embodiments, the data retrieval module may retrieve the historical data for the non-overlapping geographical tile reference from the distributed ledger. In some embodiments, the data retrieval module may further retrieve domain specific data, previously measured data from neighboring test sites, and geographical knowledge for the non-overlapping geographical tile. In some embodiments, the intermediate verification layer may further comprise a world state database that stores a current state of a plurality of assets in the distributed ledger.

According to embodiments of the present disclosure, a system for validating chemical data comprising a cloud application, a sensing device, and a mobile data processing system. The cloud application may be adapted to receive a sensor captured result, apply the sensor captured result to a domain-specific statistical model of expected range of variability of measured results to extract a distribution of expected sensor values, calculate a distribution of expected sensor values, applying the sensor captured result, compute a confidence value in the sensor captured result using the domain-specific statistical model, validate the confidence value against a required threshold of confidence; and append the sensor captured result to a blockchain. The sensing device may comprise a Universal Unique ID and a sensor element that generates the sensor captured result. The sensing device may be made of paper and performs chemical measurement of the sample using colorimetric reagents. The mobile data processing system device may be adapted to digitize the sensor captured result, capture a geographic reference and a temporal reference associated with the sensor captured result, and transmit the sensor captured result, the geographic reference, and the temporal reference to the cloud application.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
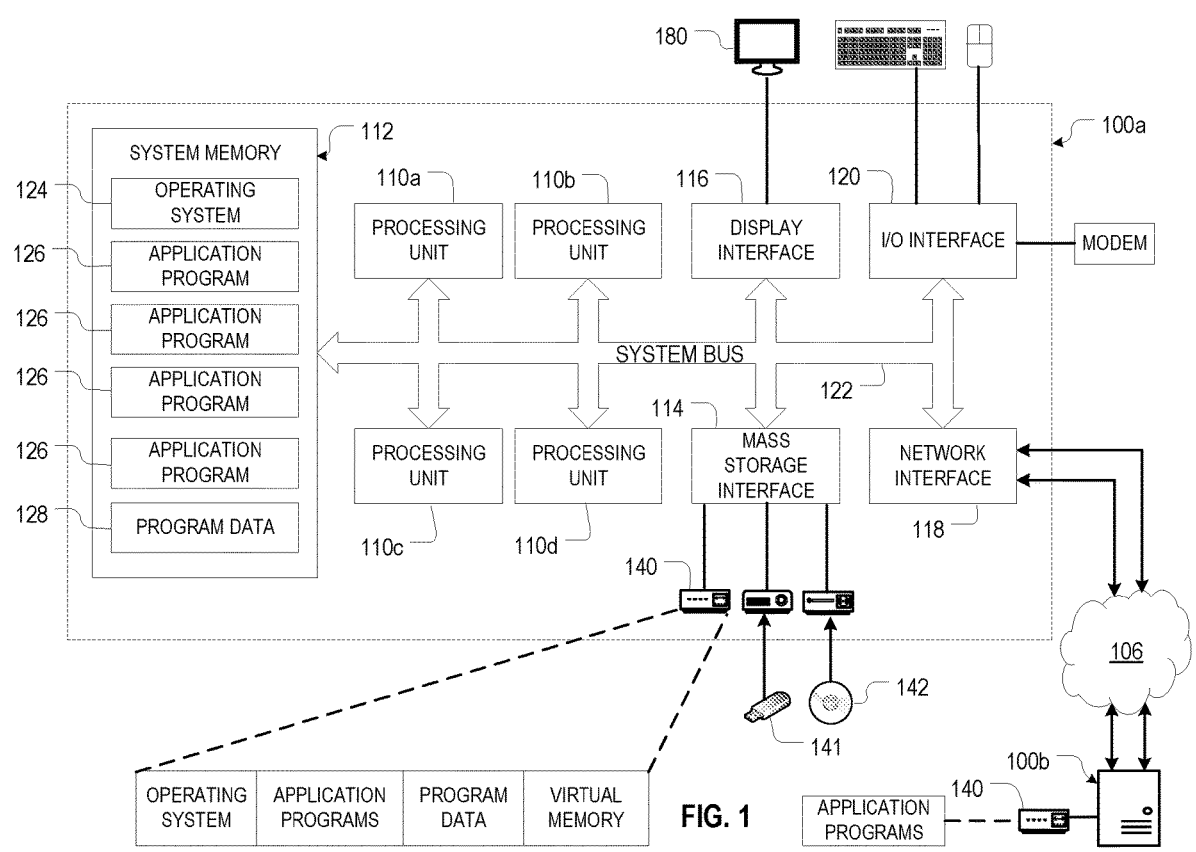
FIG. 1 illustrates an embodiment of a data processing system (DPS), consistent with some embodiments.

While the invention is amenable to various modifications and alternative forms, specifics thereof have been shown by way of example in the drawings and may be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to validating test results; more particular aspects relate to validating test results using a blockchain network. While the present disclosure is not necessarily limited to such applications, various aspects of the disclosure may be appreciated through a discussion of various examples using this context.

Advances in computing technology are currently enabling the widespread use of measurement and sensing technology in the home, supply chain, agricultural, scientific, medical, and industrial environments. Some of this technology may be in the form of a kit that requires user interaction in a data collection phase, a data analysis phase, or both. Common examples of kits include soil analysis (e.g., moisture, compactness, or chemical nutrients), leaf analysis, blood glucose test strips and meters, blood pressure monitor, etc. Increasingly, this technology may also be in the form of remotely operated sensors, leveraging technologies such as "Internet of Things" (IoT) devices, satellites, drones, thermometers, light sensors, flow meters, and the like.

The IoT, in turn, generally refers to a network of special purpose computing systems e.g., devices, vehicles, signs, buildings, and other objects embedded with electronics, software, sensors, and/or actuators, plus network connectivity, that may enable these systems to collect and exchange data with other IoT devices and/or computer systems. The IoT allows those objects to be sensed and/or controlled remotely across existing network infrastructure, creating opportunities for more direct integration of the physical world into computer-based systems, resulting in improved efficiency, accuracy, and economic benefits, in addition to reduced human intervention. When objects in the physical world are augmented with IoT sensors and actuators, the combination becomes an instance of the more general class of cyber-physical systems, also encompassing technologies such as smart grids, virtual power plants, smart homes, intelligent transportation, and smart cities.

Many systems and applications that rely on the data collected by kits and/or sensors require additional verification of accuracy and credibility. In some cases, this may be because the tests are still difficult to perform correctly and/or consistently. In other cases, test results may be inaccurate due to equipment failure or deliberate tampering. In still other cases, middlemen systems are required certify certain test results, such as those commonly used in food and medical supply chains.

These additional verifications, however, are costly and still may not entirely protect the relevant stakeholders. For example, when a food retailer outsources agronomic reports to a third-party testing company, the food retailers often can only rely on trustworthiness of that company, which could bring risk of falsification or be subject to differences in certificate standards between regions or industries. As a result, the food retailer is exposed to reputation impacts and potentially large losses in the event of a mistake or scandal. This can be a particular issue when the underlying product is grown in one jurisdiction and delivered, across international borders, to another jurisdiction.

Accordingly, one feature and advantage of some embodiments of this disclosure is that they may provide data-trusted test results that can document a test record without the need to rely on a human-trusted third party to certify the data results. Another feature and advantage of some embodiments is they may increase data confidence in test measurements by submitting the results to a blockchain, which avoids database tampering and may include also include a validation layer. This validation layer may occur before submission to the blockchain. The validation layer may include a domain-specific validation method, such as a trained artificial intelligence (AI) model, to predict a likely progression of prior measurement records and compare to the new measurement to compute a confidence score. The domain-specific validation method may account for domain specific variables, from both current and historical records, and from current and neighboring measuring sites.

In some embodiments of the disclosure, the validation layer may include an intermediate credibility checking layer for geolocation-dependent sensor data prior to submitting to a blockchain. The intermediate credibility checking layer may automatically receive a universally unique identifier (UUID) for a field test result (e.g., one particular chemical test strip), a digitization of the test results (e.g., a photograph of the chemical test strip taken by a mobile software application executing on a smart-phone or chemical concentration estimation from the mobile software application), and geo-reference data for that test result. The intermediate credibility checking layer may then automatically identify a non-overlapping geographical tile reference for the test result, retrieve historical data of current and neighboring tiles from the blockchain, and then apply a domain-specific validation method that accounts for the current and historical sensor data from the current and neighboring measuring sites, as well as the domain specific knowledge (e.g., current and/or historical weather records), to calculate a likely progression of the test result. The intermediate credibility checking layer may then automatically compare to the new test result to compute a confidence score. If the confidence score for the new test result is within the protocol for this particular testing plan, then the new test result may be appended to the distributed ledger of the blockchain and/or a thread of the blockchain. In this way, some embodiments may provide a validation method for input test data transactions prior to appending to blockchain and/or blockchain thread that is specific to geography-sensitive data that combines unique identifiers, geo-location, historical and neighboring test data, domain-specific knowledge (e.g., weather records), and data checking based on domain specific statistical models to create a data trusted test result that can represent a test record without the need of a human-trusted third party to certify the test results.

Data Processing System

FIG. 1 illustrates an embodiment of a data processing system (DPS) 100a, consistent with some embodiments. The DPS 100a in this embodiment may be implemented as a personal computer; server computer; portable computer, such as a laptop or notebook computer, PDA (Personal Digital Assistant), tablet computer, or smart phone; processors embedded into a larger devices, such as an automobile, airplane, teleconferencing system, appliance; smart devices; or any other appropriate type of electronic device. Moreover, components other than or in addition to those shown in FIG. 1 may be present, and that the number, type, and configuration of such components may vary. Moreover, FIG. 1 only depicts the representative major components of the DPS 100a, and individual components may have greater complexity than represented in FIG. 1.

The data processing system 100a in FIG. 1 comprises a plurality of central processing units 110a-110d (herein generically referred to as a processor 110 or a CPU 110) connected to a memory 112, a mass storage interface 114, a terminal/display interface 116, a network interface 118, and an input/output ("I/O") interface 120 by a system bus 122. The mass storage interface 114 in this embodiment connect the system bus 122 to one or more mass storage devices, such as a direct access storage device 140, universal serial bus ("USB") storage device 141, or a readable/writable optical disk drive 142. The network interfaces 118 allow the DPS 100a to communicate with other DPS 100b over the communications medium 106. The memory 112 also contains an operating system 124, a plurality of application programs 126, and program data 128.

The data processing system 100a embodiment in FIG. 1 is a general-purpose computing device. Accordingly, the processors 110 may be any device capable of executing program instructions stored in the memory 112 and may themselves be constructed from one or more microprocessors and/or integrated circuits. In this embodiment, the DPS 100a contains multiple processors and/or processing cores, as is typical of larger, more capable computer systems; however, in other embodiments the computing systems 100a may comprise a single processor system and/or a single processor designed to emulate a multiprocessor system. Further, the processors 110 may be implemented using a number of heterogeneous data processing systems 100a in which a main processor is present with secondary processors on a single chip. As another illustrative example, the processor 110 may be a symmetric multiprocessor system containing multiple processors of the same type.

When the data processing system 100a starts up, the associated processor(s) 110 initially execute the program instructions that make up the operating system 124, which manages the physical and logical resources of the DPS 100a. These resources include the memory 112, the mass storage interface 114, the terminal/display interface 116, the network interface 118, and the system bus 122. As with the processor(s) 110, some DPS 100a embodiments may utilize multiple system interfaces 114, 116, 118, 120, and busses 122, which in turn, may each include their own separate, fully programmed microprocessors.

Instructions for the operating system, applications and/or programs (generically referred to as "program code," "computer usable program code," or "computer readable program code") may be initially located in the mass storage devices 140, 141, 142, which are in communication with the processors 110 through the system bus 122. The program code in the different embodiments may be embodied on different physical or tangible computer readable media, such as the system memory 112 or the mass storage devices 140, 141, 142. In the illustrative example in FIG. 1, the instructions are stored in a functional form of persistent storage on the direct access storage device 140. These instructions are then loaded into the memory 112 for execution by the processor 110. However, the program code may also be located in a functional form on the computer readable media 142 that is selectively removable and may be loaded onto or transferred to the DPS 100a for execution by the processor 110.

The system bus 122 may be any device that facilitates communication between and among the processors 110; the memory 112; and the interfaces 114, 116, 118, 120. Moreover, although the system bus 122 in this embodiment is a relatively simple, single bus structure that provides a direct communication path among the system bus 122, other bus structures are consistent with the present disclosure, including without limitation, point-to-point links in hierarchical, star or web configurations, multiple hierarchical buses, parallel and redundant paths, etc.

The memory 112 and the mass storage devices 140, 141, 142 work cooperatively to store the operating system 124, the application programs 126, and the program data 128. In this embodiment, the memory 112 is a random-access semiconductor device capable of storing data and programs. Although FIG. 1 conceptually depicts that device as a single monolithic entity, the memory 112 in some embodiments may be a more complex arrangement, such as a hierarchy of caches and other memory devices. For example, the memory 112 may exist in multiple levels of caches, and these caches may be further divided by function, so that one cache holds instructions while another holds non-instruction data, which is used by the processor or processors. Memory 112 may be further distributed and associated with different processors 110 or sets of processors 110, as is known in any of various so-called non-uniform memory access (NUMA) computer architectures. Moreover, some embodiments may utilize virtual addressing mechanisms that allow the DPS 100a to behave as if it has access to a large, single storage entity instead of access to multiple, smaller storage entities such as the memory 112 and the mass storage device 140, 141, 142.

Although the operating system 124, the application programs 126, and the program data 128 are illustrated as being contained within the memory 112, some or all of them may be physically located on different computer systems and may be accessed remotely, e.g., via the communications medium 106, in some embodiments. Thus, while the operating system 124, the application programs 126, and the program data 128 are illustrated as being contained within the memory 112, these elements are not necessarily all completely contained in the same physical device at the same time and may even reside in the virtual memory of other DPS e.g., DPS 100b.

The system interfaces 114, 116, 118, 120 support communication with a variety of storage and I/O devices. The mass storage interface 114 supports the attachment of one or more mass storage devices 140, 141, 142, which are typically rotating magnetic disk drive storage devices, a solid-state storage device (SSD) that uses integrated circuit assemblies as memory to store data persistently, typically using flash memory, or a combination of the two. However, the mass storage devices 140, 141, 142 may also comprise other devices, including arrays of disk drives configured to appear as a single large storage device to a host (commonly called RAID arrays) and/or archival storage media, such as hard disk drives, tape (e.g., mini-DV), writeable compact disks (e.g., CD-R and CD-RW), digital versatile disks (e.g., DVD, DVD-R, DVD+R, DVD+RW, DVD-RAM), holography storage systems, blue laser disks, IBM Millipede devices, and the like.

The terminal/display interface 116 is used to directly connect one or more display units, such as monitor 180, to the data processing system 100a. These display units 180 may be non-intelligent (i.e., dumb) terminals, such as an LED monitor, or may themselves be fully programmable workstations used to allow IT administrators and customers to communicate with the DPS 100a. Note, however, that while the display interface 116 is provided to support communication with one or more display units 180, the computer systems 100a does not necessarily require a display unit 180 because all needed interaction with customers and other processes may occur via network interface 118.

The communications medium 106 may be any suitable network or combination of networks and may support any appropriate protocol suitable for communication of data and/or code to/from multiple DPS 100a, 100b. Accordingly, the network interfaces 118 can be any device that facilitates such communication, regardless of whether the network connection is made using present day analog and/or digital techniques or via some networking mechanism of the future. Suitable communication media 106 include, but are not limited to, networks implemented using one or more of the "InfiniBand" or IEEE (Institute of Electrical and Electronics Engineers) 802.3x "Ethernet" specifications; cellular transmission networks; wireless networks implemented one of the IEEE 802.11x, IEEE 802.16, General Packet Radio Service ("GPRS"), FRS (Family Radio Service), or Bluetooth specifications; Ultra-Wide Band ("UWB") technology, such as that described in FCC 02-48; or the like. Those skilled in the art will appreciate that many different network and transport protocols can be used to implement the communications medium 106. The Transmission Control Protocol/Internet Protocol ("TCP/IP") suite contains suitable network and transport protocols.

Cloud Computing

Figure 2:
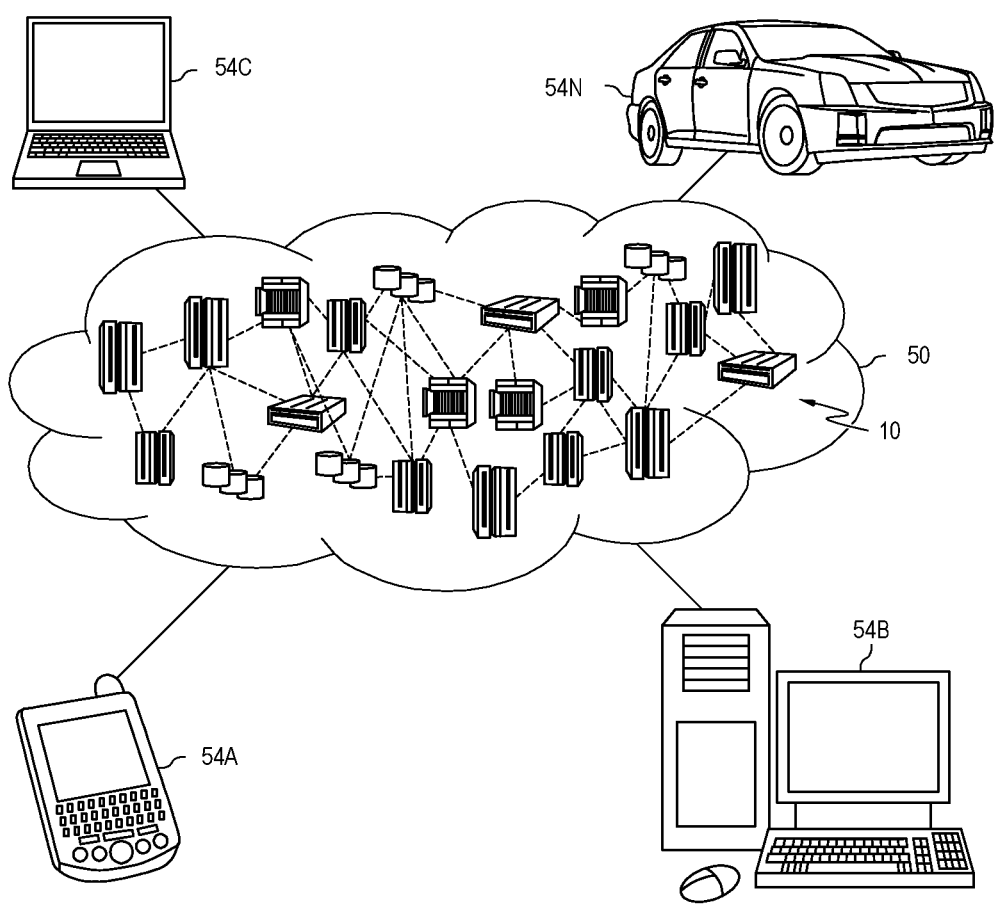
FIG. 2 depicts a cloud computing environment, consistent with some embodiments.

FIG. 2 illustrates a cloud environment containing one or more DPS 100a, consistent with some embodiments. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active customer accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited customer-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
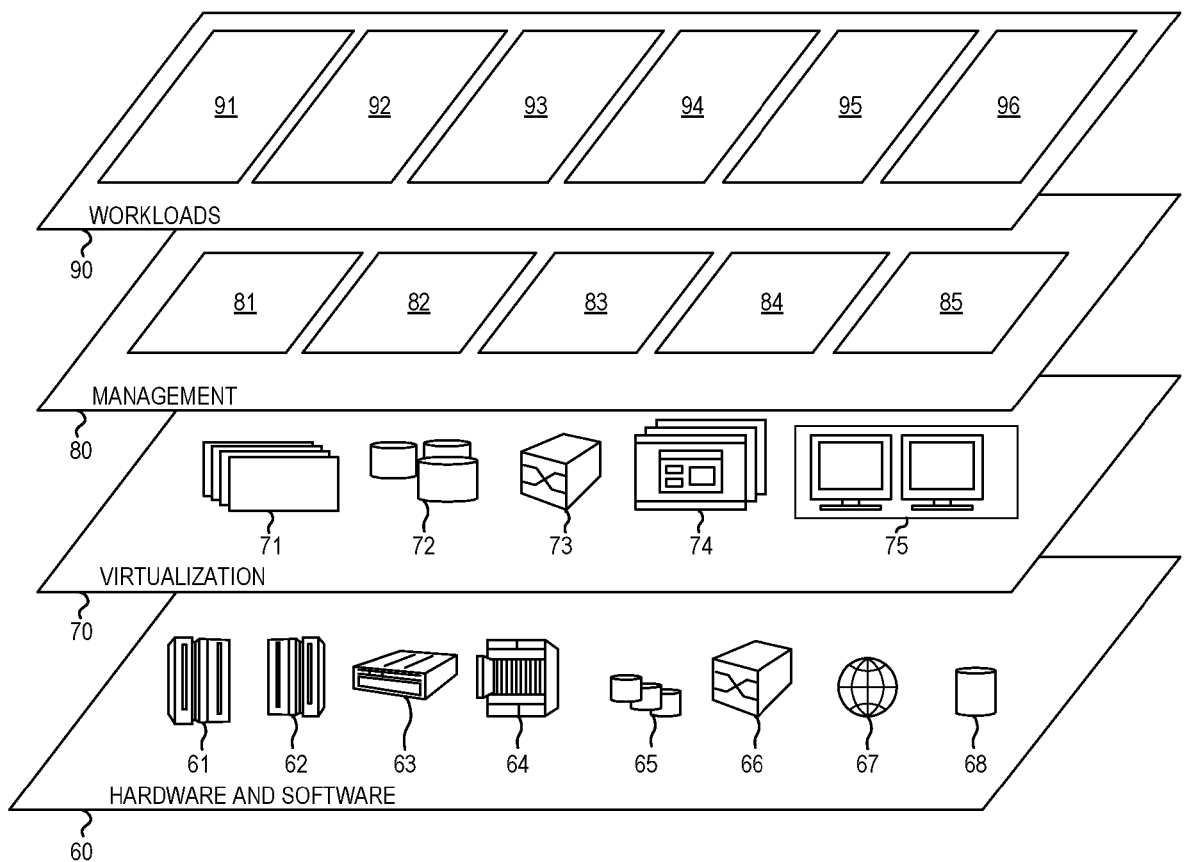
FIG. 3 depicts abstraction model layers, consistent with some embodiments.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. Customer portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a blockchain service 96.

Data Collection System

Figure 4:
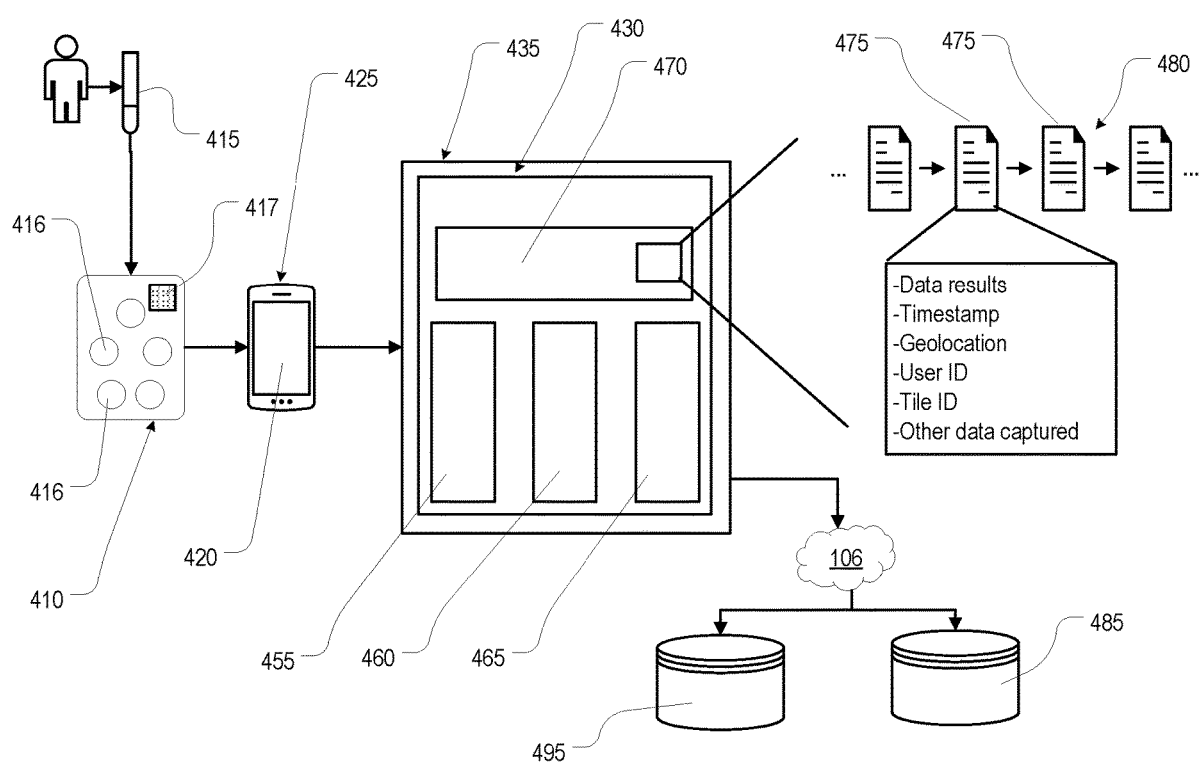
FIG. 4 is a system diagram of a data collection system, consistent with some embodiments

FIG. 4 is a system diagram of a data collection system 400, consistent with some embodiments. FIG. 4 includes a sensing device 410, a mobile application (app) 420 executing on a smartphone or portable computing device 425, and a blockchain cloud application 430 executing on a cloud-based DPS 435, such as DPS 100*a*.

The sensing device 410 in this embodiment may be any device capable of performing a desired test/analysis on a sample 415 in the field and associating the test with a UUID. In some embodiments, the sensing device 410 may be capable of performing the entire test/analysis and outputting test data. In other embodiments, the sensing device 410 may only be capable of producing intermediate data to be further analyzed by another system (e.g., a test strip with one or more test sites 416 and a printed quick response (QR) code, barcode or text to be read using Optical Character Recognition (OCR) 417 that may be analyzed by the mobile application 420). One example sensing device 410 is a paper test strip that performs chemical measurement of a sample using colorimetric reagents printed thereon.

The mobile app 420 in some embodiment may be executing on a smartphone, tablet, or other portable computing device, such as laptop computer. The mobile application 420 may digitize the test data from the sensor device 410 (e.g., capture an image of the sensing device 410), capture test time and geo-location information (e.g., using services provided by the smartphone 425), perform identification of the test taker (e.g., by user login), obtain sensing device 410 identification (e.g., by a QR code in the captured image), and other supplemental information (card picture, card specs, user inputs, etc.) The mobile app 420 also performs an analysis of the digitized sensor data results, if required (e.g., correlate a test strip color into a pH value). The mobile app 420 may then upload the collected information, and optionally the analysis, to the blockchain application 430.

The blockchain application 430 in this embodiment may include a geolocation module 455, a data retrieval module 460, a validation module 465, a blockchain transaction data composer and chaincode interfacing module 470, one or more blockchain distributed ledger blocks 475 in a blockchain 480. The blockchain application 430 may also be adapted to query a world state database (DB) 485 and a domain specific knowledge database 495 over a network 106.

The geolocation module 455 in this embodiment may be a software component that has a geographical representation of a target area (e.g., a farm field) in non-overlapping tiles or using geofences. The geolocation module 455 may determine a tile identifier (ID) of a current sensor measurement using the geo-location information from the sensing device 410 and/or mobile app 420. The geolocation module 455 in some embodiments may include a geographical reference database 457 to convert between GPS coordinates, etc. and tile IDs.

The data retrieval module 460 in this embodiment may be a software component that uses the Tile IDs generated by the geo-location module 455 to retrieve current and historic sensor data for the target area from the blockchain ledger.

The validation module 465 in this embodiment may be a software component that uses the historical and neighboring tiles' records retrieved by the data retrieval module 460, plus domain specific knowledge data (e.g., historical weather records) from the knowledge database, to compute a confidence level on sensor measurement collected by the sensing device 410

The blockchain transaction data composer and chaincode interfacing module 470 in this embodiment may be a software component that orchestrates, formats, and works as a data interface with the blockchain 480. That blockchain 480 includes one or more blockchain distributed ledger blocks 475, which may contain all the attributes of the measurement e.g., the test ID, the user ID, the geolocation information, the TILE ID, the sensor results, the time-stamp, and other relevant attributes, such as the captured image, the test equipment specs, the users' inputs, etc.

The world state database 485 in this embodiment also may be a part of the blockchain 480, and stores a current state of all blockchain assets. The world state database 485 may also be used to store, for each transaction or test, the test ID, the associated tile ID, the set of neighboring tiles IDs, the date, the test data, and other supplemental information.

Testing Protocol

Figure 5A:
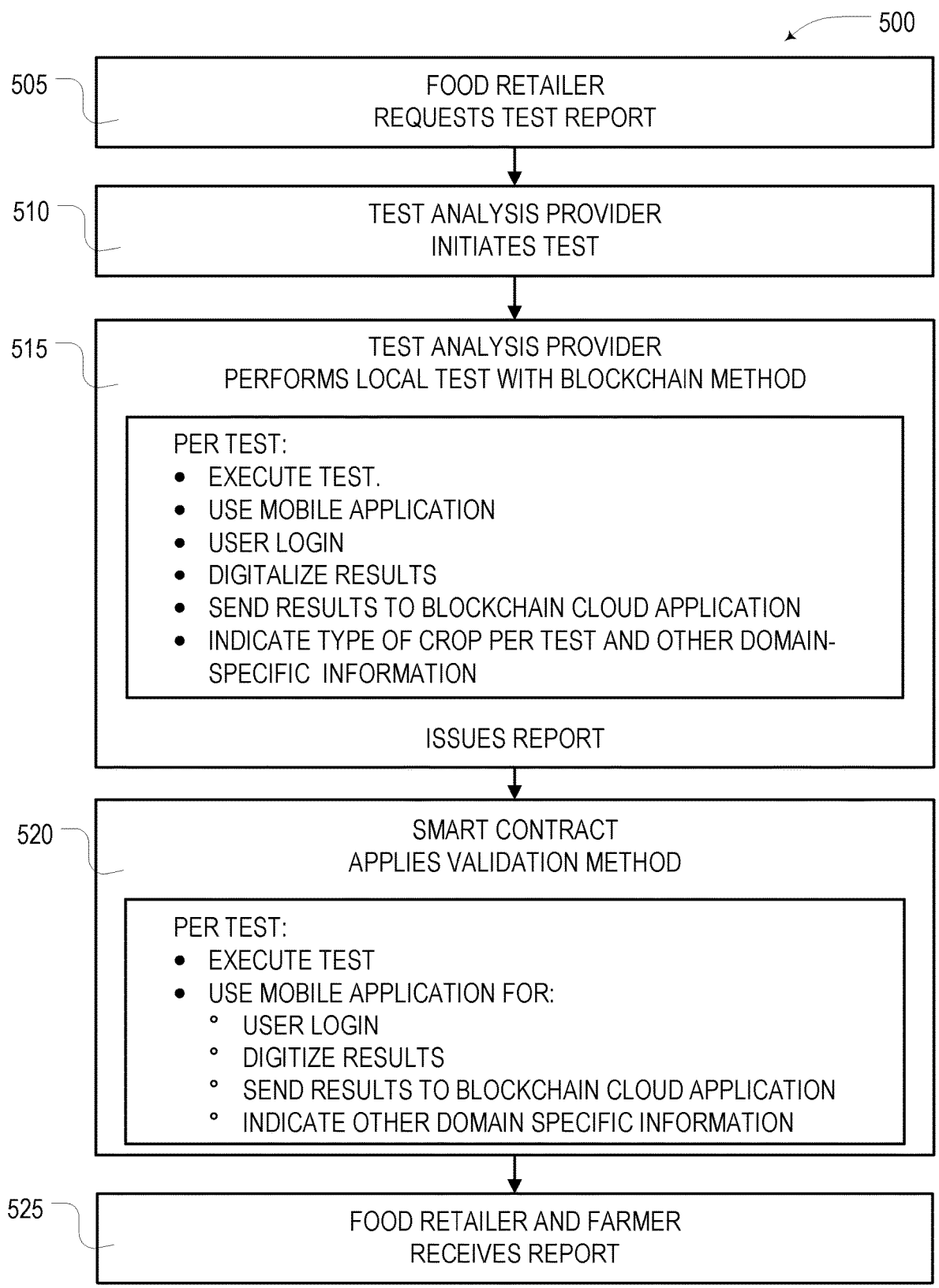
FIG. 5A is a flow chart illustrating the data collection system in operation, as applied to an illustrative example of an agricultural supply chain and consistent with some embodiments of the disclosure.

FIG. 5A is a flow chart illustrating the data collection system 500 in operation, as applied to an illustrative example of an agricultural supply chain and consistent with some embodiments of the disclosure. Those skilled in the art will recognize, however, that the disclosure is not limited to this illustrative example, and instead, may be applied to any testing protocol, including those using manually collected data and/or automatically collected data.

In this illustrative example, a food retailer (e.g., a coffee store) may subcontract specialized agronomic companies to create reports on the sustainability and productivity of small coffee producers. The primary stakeholders in this test include the coffee growers, the test analysis providers, and the coffee retailers. Other potential stockholders may include the land/farm owners, fertilizer and other chemical companies, purchasing/marketing cooperatives, and government agencies.

The landowner or cooperative in this illustrative example may engage the farmer to perform soil test at a number of locations. At each location, the farmer may take a sample, perform the test, take a geo-tagged picture of the test results, and then transmit the results to a cloud application. As a result, each test may be automatically tagged with its location, capture time, and/or sequence number, with each combination of tags being unique. The location can be a GS1 Global Location Number (GLN), based on GPS coordinates or global farm number, a grid number, or other location signifier. The time tag, in turn, may be a code indicative of the current date and time. The sequence tag may be any indicative of one of a series of transactions for the sampling location. That is, for each location, there will a chain of linked transactions, each corresponding to a soil health test at a particular time.

The cloud application in this illustrative example may create a validation test for this specific type of test using domain specific knowledge and the linked series of tests at this particular site, as well as those taken at neighboring sites. In some embodiments, this may be an artificial intelligence (AI) based test trained using that historical data. The new test results may be input into the validation test, and its output may be used to compute a confidence score for the new test results. If the test appears reasonable i.e., has a high confidence score, the cloud application may then submit the new test results to the blockchain. In some embodiments, this may include signing the new test results pursuant to a smart contract.

In FIG. 5A, the food retailer may request a test report at operation 505. In response, a test analysis provider may initiate the test at operation 510. This may include collecting physical samples at a variety of locations in a farm field. The test analysis provider may then execute and validate the local tests with blockchain at operation 515. This may include chemically analyzing the samples using a mobile testing kit and digitizing the results (including the UUID) using the sensing device 410 and the mobile app 420. Using also mobile app 420, the test analysis provider may append their personal user identifier (e.g., user login) and any relevant domain-specific information (e.g., the type of crop being grown, current weather, recent weather events, geographical knowledge, farming knowledge, historical irrigation data, most recent fertilization date, etc.) to the test results. The test analysis provider, from the mobile app 420, may additionally send the resulting data to the blockchain cloud application 430.

At operation 520, the blockchain cloud application 430 may execute a smart contract that applies a validation method to the test. In this illustrative example, the smart contract may, per test: (i) authenticate the UUID associated with the sensing device 410 and/or mobile app 420; (ii) identify a geographical tile at which the test data was collected; (iii) retrieve historical and domain-specific (e.g., historical weather) records about the geographical tile, as well as neighboring tiles; (iv) validate the test results; (v) update the distributed ledger 475 of the blockchain 480 and the world state database 485; and (vi) issue a report about the validity of the test results. This report, received by the food retailer and the farmer at operation 525, may be used to ensure the quality of the supplier (e.g., the farmer in this illustrative example), monitor the condition of the product as it moves through the supply chain, document compliance with contractual and market commitments of the stake holders, and automatically trigger payments to and from the various stakeholders.

Figure 5B:
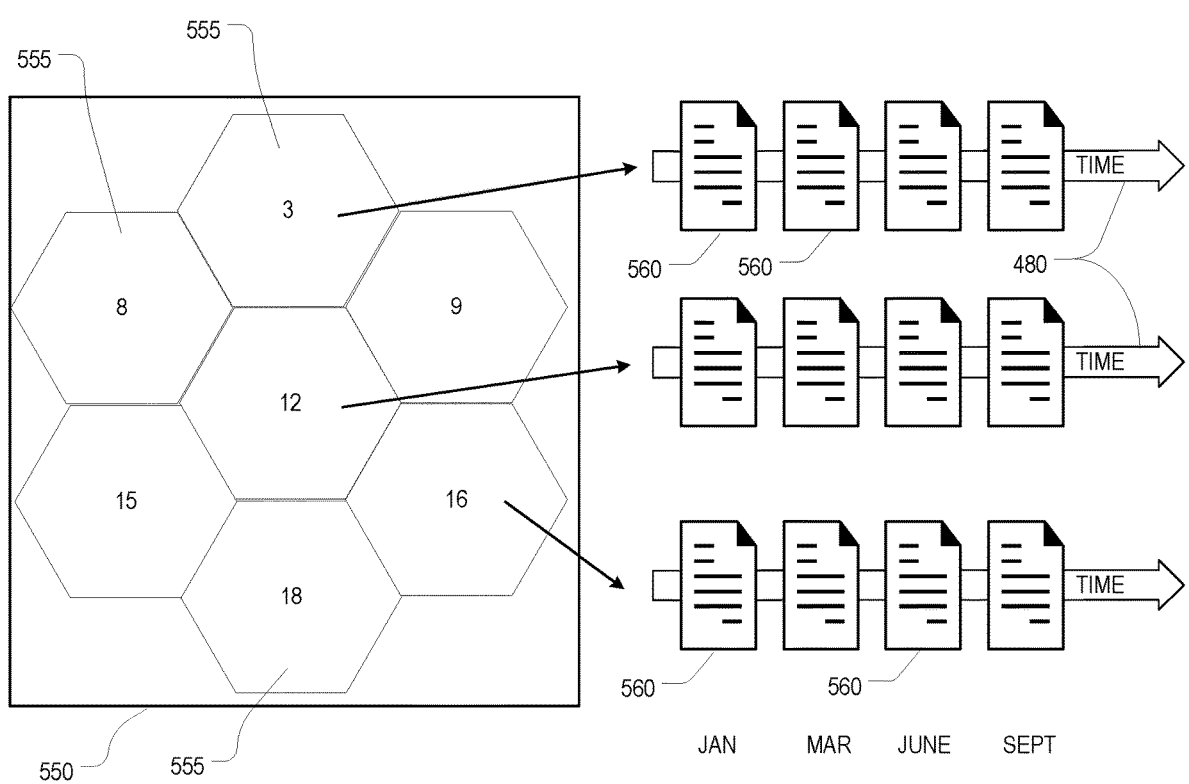
FIG. 5B is a system diagram of the testing protocol, as applied to the illustrative example of an agricultural supply chain in FIG. 5A, consistent with some embodiments of the disclosure.
Figure 6A:
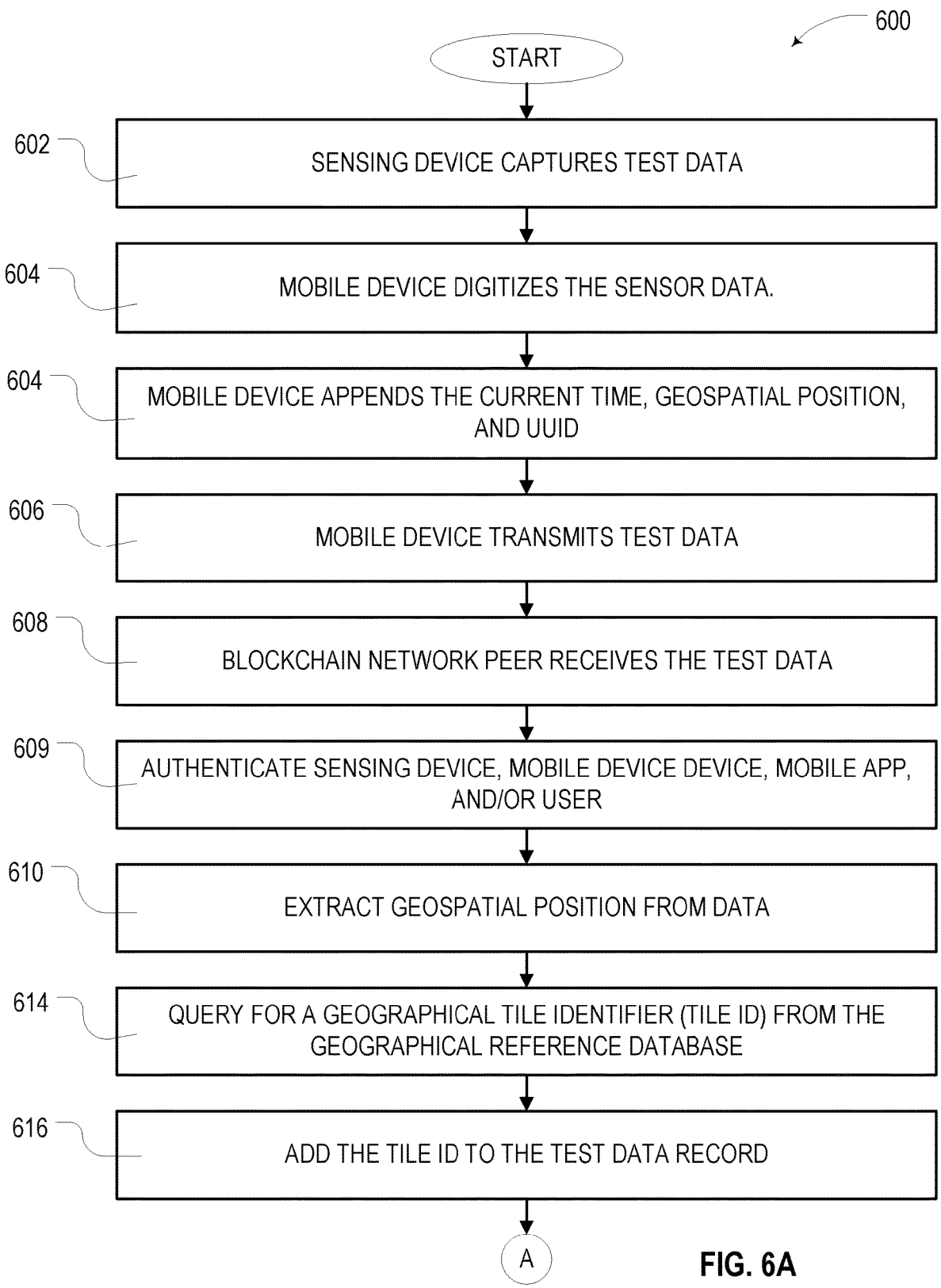
FIGS. 6A-D are a flow chart illustrating one method of validating new test results, consistent with some embodiments.
Figure 6B:
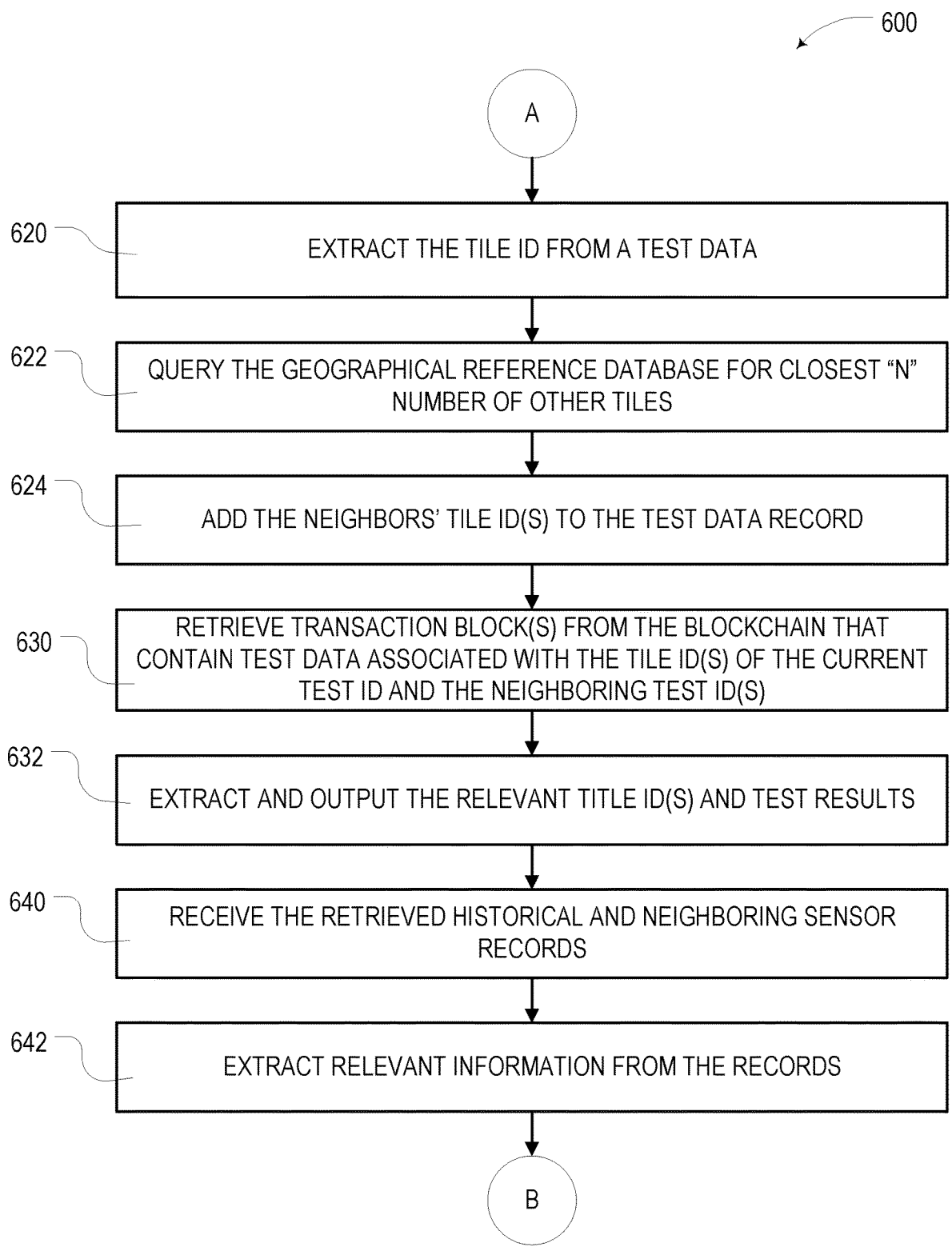
Figure 6C:
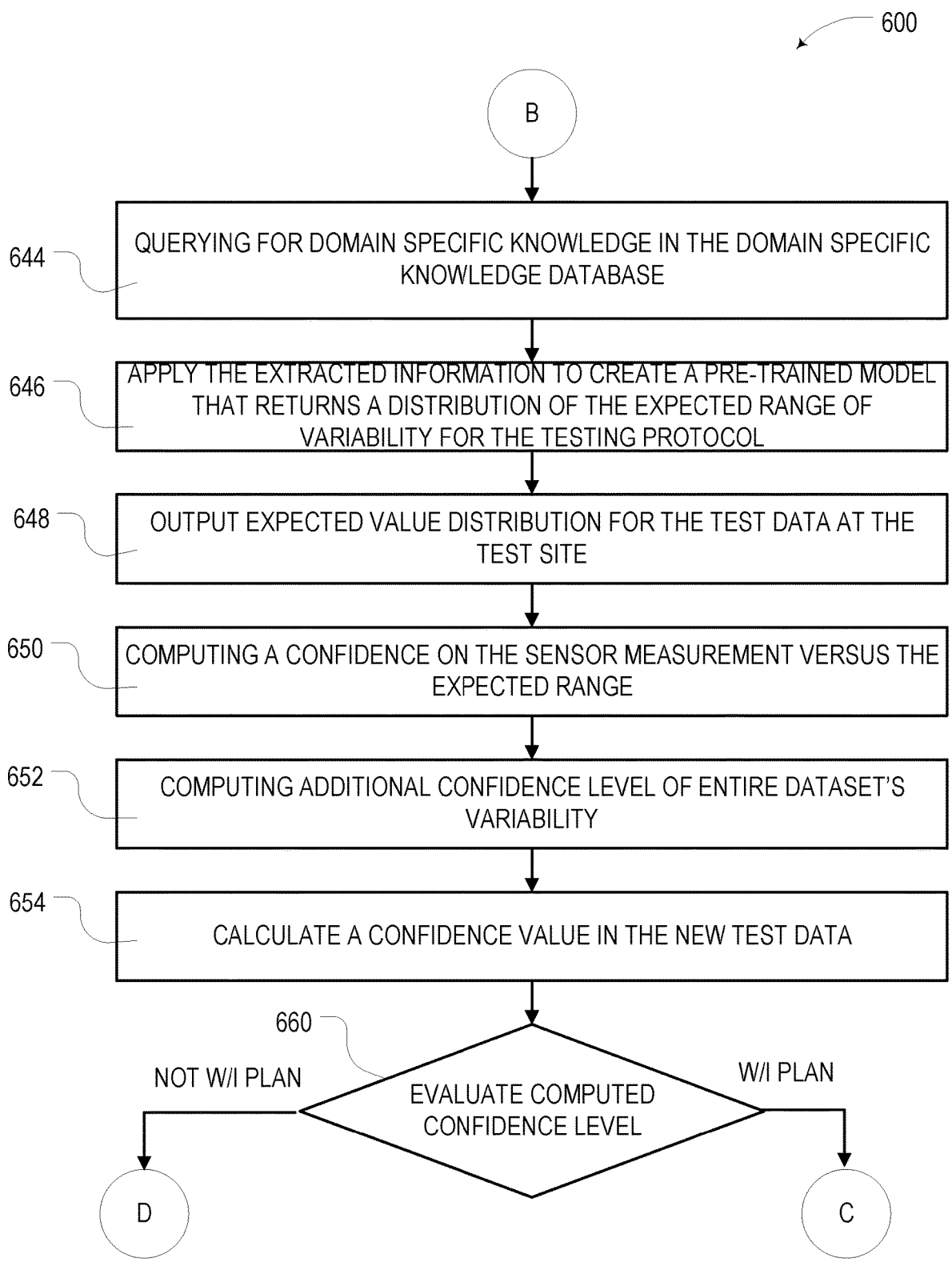
Figure 6D:
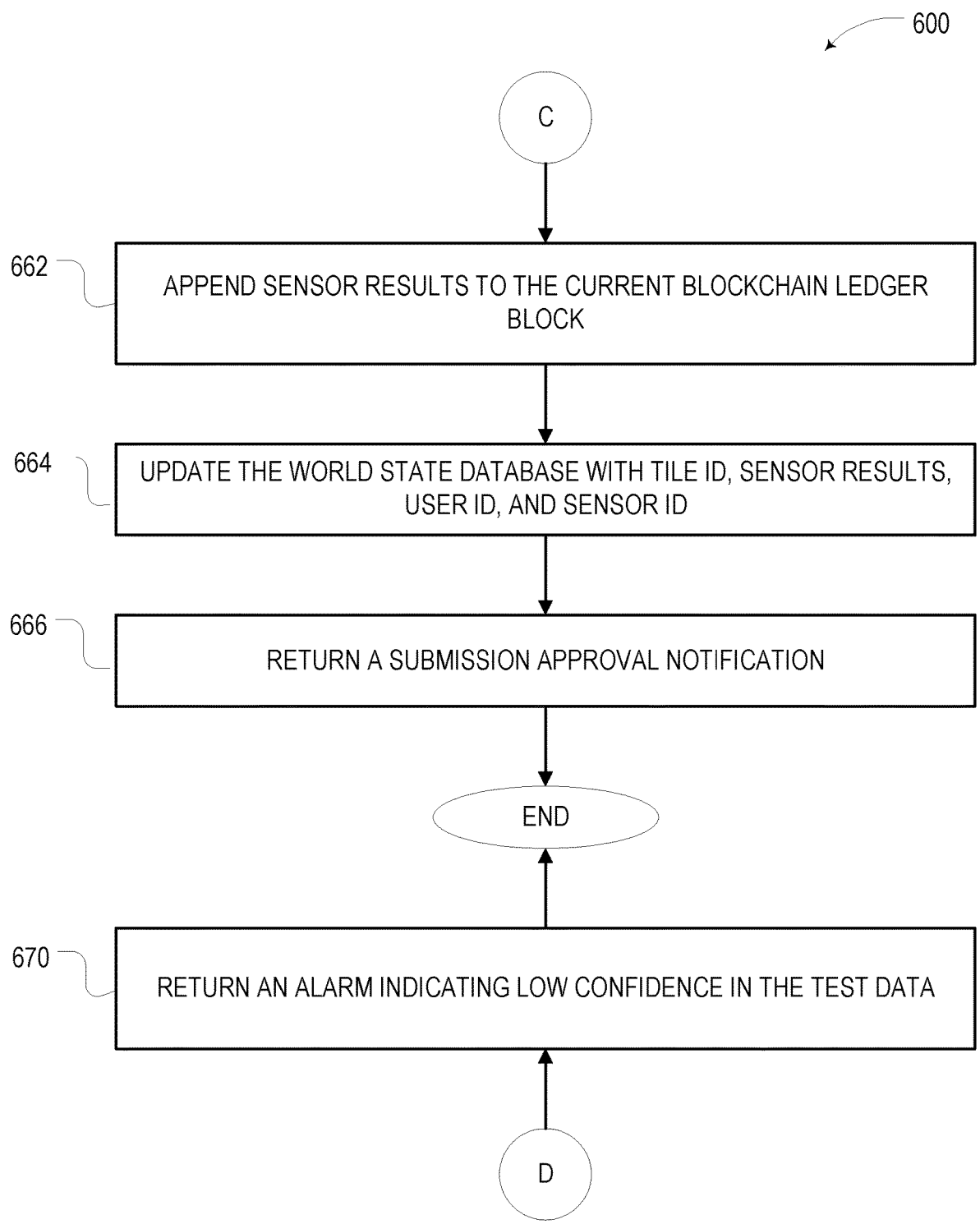

FIG. 5B is a system diagram of the testing protocol, as applied to the illustrative example of an agricultural supply chain in FIG. 5A, consistent with some embodiments of the disclosure and with only some labeled for clarity. In this system, a farm 550 is divided up into a number of test tiles 555, such as a hex grid for more consistent distances or a rectangular grid for easier identification. Each test tile 555 has been given a unique Tile Identifier (Tile ID). The tile identifier may be a GS1 Global Location Number (GLN), be based on global positioning (GPS, Glonass, Galileo, etc.) coordinates, based on a global farm number, etc. For each test tile 555, there may be a chain of transactions 560 on the blockchain 480, each corresponding to a soil health test. As a result, each sampling location may have a series of linked tests taken at various times.

Test Validation

FIGS. 6A-D is a flow chart illustrating one method 600 of validating new test results, consistent with some embodiments. At operation 602, the sensing device 410 captures one or more data points, for example, performing one or more chemical soil analysis of a soil sample. At operation 603, the mobile device 420 digitizes the sensor data, for example, by capturing the image of sensor device 410 and extracting features that represent the captured data, for instance, by image processing techniques. At operation 604, the mobile device 420 may append the time when the test was performed, the geospatial position of the sensing device 410 at the time of the test, and a UUID for the test to the sensor data. The UUID in some embodiments may be integrated into the sensing device 410 in some embodiments (e.g., in a QR code) and captured as part of the digitization. In other embodiments, the UUID may be generated by the mobile device 420 using the time and location as inputs. At operation 606, the mobile device 420 transmits the test data (e.g., the sensor data, the current time, the geospatial position, and the UUID) to the blockchain cloud application 430.

A blockchain network peer, such as DPS 100a, may receive the test data from the mobile application 420 at operation 608. This information may be organized using an JSON (JavaScript Object Notation) or an XML (Extensible Markup Language) data structure. Table 1 is an illustrative example of one such data in JSON structure:

TABLE 1

{
 "Test ID": 12345,
 "USER ID": "bob@agrocompany.com",
 "GEOLOCATION":
  {
   "LATITUDE": "−23.580812",
   "LONGITUDE":"−46.640928"
  },
 "RESULTS":
  {
   "pH": "5.2"
  }
}

The blockchain peer may then authenticate the UUID, represented in Table 1 as "Test ID", associated with the sensing device 410 and/or mobile application 420 at operation 609. This may include comparing the transmitted UUID to a list of devices 425 that have been previously authorized and calibrated for this test plan. Operation 609 may also include authenticating the mobile device 425, the mobile app 420, and/or the user that conducted the test.

At operations 610-616, the geolocation module 455 may identify the tile ID from the transmitted geospatial position. This may include extracting geospatial position from the test data at operation 610 (e.g., the latitude and longitude information from the illustrative example in Table 1), and then using the extracted geospatial position to query for a geographical tile identifier (tile ID) from the geographical reference database 457 at operation 614. Continuing the illustrative example, if the geographical reference database 457 contains the information in Table 2:

TABLE 2

| #REG | TILE ID | LAT | LONG |
|------|---------|--------|--------|
| 980 | 006 | −23.57 | −46.64 |
| 981 | 007 | −23.58 | −46.64 |
| 982 | 008 | −23.59 | −46.65 |

The query for the test data in Table 1 will return a Tile ID of "007" because that tile most closely matched (i.e., closest distance to) the extracted geospatial position. At operation 616, the geolocation module 455 may add the tile ID to the test data record. Continuing the illustrative example, the resulting augmented test data record is shown in Table 3:

TABLE 3

```
{
    "Test ID": 12345,
    "USER ID": "bob@agrocompany.com",
    "GEOLOCATION":
    {
        "LATITUDE": "−23.580812",
        "LONGITUDE": "−46.640928"
    },
    "RESULTS":
    {
        "pH": "5.2"
    }
    "Tile ID": 007
}
```

At operations 620-624, the geolocation module 455 may determine the tile IDs of neighboring tiles to the test location using additional queries of the geographical reference database 457. In some embodiments, the geolocation module 455 may extract the Tile ID (associated with the test data at operation 616) and/or the geospatial position from a test data record at operation 620. Next, at operation 622, geolocation module 455 may then query the geographical reference database 457 for closest "N" number of other tiles to the extracted Tile ID and/or geospatial position, where "N" may be specified by the testing protocol. Alternatively, records for each Tile ID in the geographical reference database 457 may contain a list of closes neighbors. The geolocation module 455 may add the neighbors' tile ID(s) to the test data record at operation 624.

Next, at operations 630-632, the data retrieval module 460 may retrieve the current and historical testing records for the current and neighboring tiles from blockchain ledger 475 using the tile ID(s) found at operations 620-624. In one embodiment, the data retrieval module 460 may retrieve one or more transaction block(s) 475 from the blockchain 480 that contain test data associated with the Tile ID(s) of the current test ID and the neighboring test ID(s) at operation 630. Continuing the illustrative example, Table 4 contains a sample blockchain transaction record including example fields with information regarding the sensor data at the measurement location, according to the present disclosure:

TABLE 4

Sensor data: (e.g., chemical data: concentrations of Nitrogen, Phosphorous, Potassium, Calcium, Magnesium, Boron, Copper, Aluminum, pH, etc.)
Geolocation: (e.g., data regarding to the location of measurement site, for instance, GPS coordinates)
User ID: (e.g., identification of the technician who is executing the test)
Time stamp: (e.g., data regarding to time and date of the test)
Tile ID: (e.g., identification of measurement site)
Test ID: (e.g., identification of the sensor device, UUID)
Domain specific information: (e.g., farming information)
Other supplemental information: (e.g., sensing device specification, original captured image, phone model, mobile app 420 version, mapping request ID, computed confidence level, weather information, etc.)

At operation 632, the geolocation module 455 may extract and output the relevant Title ID(s) and test results. Table 5 contains possible extracted data for the illustrative example:

TABLE 5

```
{
    "result 0":
    {
        "Tile ID":"002",
        "pH":"5.0"
    },
    "result 1":
    {
        "Tile ID":"003",
        "pH":"5.4"
    },
    "result 2":
    {
        "Tile ID":"006",
        "pH":"5.0"
    },
    "result 3":
    {
        "Tile ID":"007",
        "pH":"5.2"
    },
....}
```

The validation module 465 may use the retrieved historical records, as well as a domain specific knowledge and historical weather records from the database 495, to inform validation models and to output distribution of probability of expected sensor device measurement values at operations 640-648. In some embodiments, this may include receiving the retrieved historical and neighboring sensor records at operation 640, extracting the relevant information from the records at operation 642, and then querying for domain specific knowledge in the domain specific knowledge database 495 at operation 644. Continuing the illustrative example, the validation module 465 may issue the following query:

"TILE ID": 007 and may receive the following result:

soy-05; Clay; depl. rate: 2e-5 mg/day of N, 2e-5 mg/day of K; . . . .

The validation module 465 may apply the extracted information as input to a previously trained model that returns a distribution of the expected range of variability for the testing protocol at operation 646. In some embodiments, this model may use artificial intelligence (AI) techniques, such as an adversarial neural network, deep neural network that was previously trained using data from a variety of geographical regions, the data comprising, per instance of non-overlapping tile, historical measurements and geo-location-sensitive domain-specific data extending on a plurality of non-overlapping geographical neighboring tiles, repeated over a plurality of tiles. In other embodiments, the model may be an expert model built by domain experts from the fundamental physical and chemical properties for the test. In still other embodiments, the model may combine multiple AI and expert models, with varying confidence levels assigned to each. Continuing the illustrative example, Table 6 contains the input fields of one such model comprising various domain specific entries filled with values corresponding to the target tile as well as neighboring tiles:

TABLE 6

| Tile ID | Time elapsed (days) | Topography Type | Crop Type | Crop Stage | Fertilizer Type | pH | ... |
|---|---|---|---|---|---|---|---|
| 65 | 550 | Slope | Soy | Harvest | NPK | 6.3 | ... |
| 44 | 650 | Plain | Soy | Harvest | NPK | 6.2 | ... |
| 63 | 60 | Rocky | Soy | Harvest | NPK | 5.8 | ... |
| ... | ... | ... | ... | ... | ... | ... | ... |

The validation module 465 may output expected value distribution for the test data at the test site at operation 648.

The validation module 465 may compute final confidence level on sensor data at operations 650-652. In some embodiments, this may include computing a confidence on the sensor measurement from a correlation of current measurement versus the distribution of expected test data as returned from operation 648 in operation 650, and computing additional confidence level of entire dataset's variability within normal range to check for systematic user error, device 410, 420 failure, or intentional fraud at operation 652. These two checks may be combined to calculate a final confidence value in the new test data at operation 654.

At operation 660, the system may evaluate the computed confidence level against required a confidence level threshold. If the computed confidence level is within acceptable bounds for the testing plan, then the system may append sensor results to the current blockchain ledger block 475 at operation 662; and may update the world state database 485 with tile ID, sensor results, user ID, and sensor ID at operation 664. Table 7 contains the resulting world state database 485 for the illustrative example:

the world state database 485 containing information including: the blockchain block identifier; the user identification automatically collected by the mobile application when technician logged into the app; the tile ID corresponding field or delimited area where tests are being performed; the latitude, and longitude coordinates about exactly where the test sample was collected; test date/time about when the test was performed; the sensor data, such as the chemical test results; and the UUID for the test. The system may then return a submission approval notification to the mobile application 420 and/or other stakeholders at operation 666.

If, however, the computed confidence level is outside acceptable bounds for the testing protocol, then the system may return an alarm to capturing device 410, the mobile application 420, and/or the stakeholders indicating low confidence in the test data at operation 670.

Blockchain Architecture

Figure 7A:
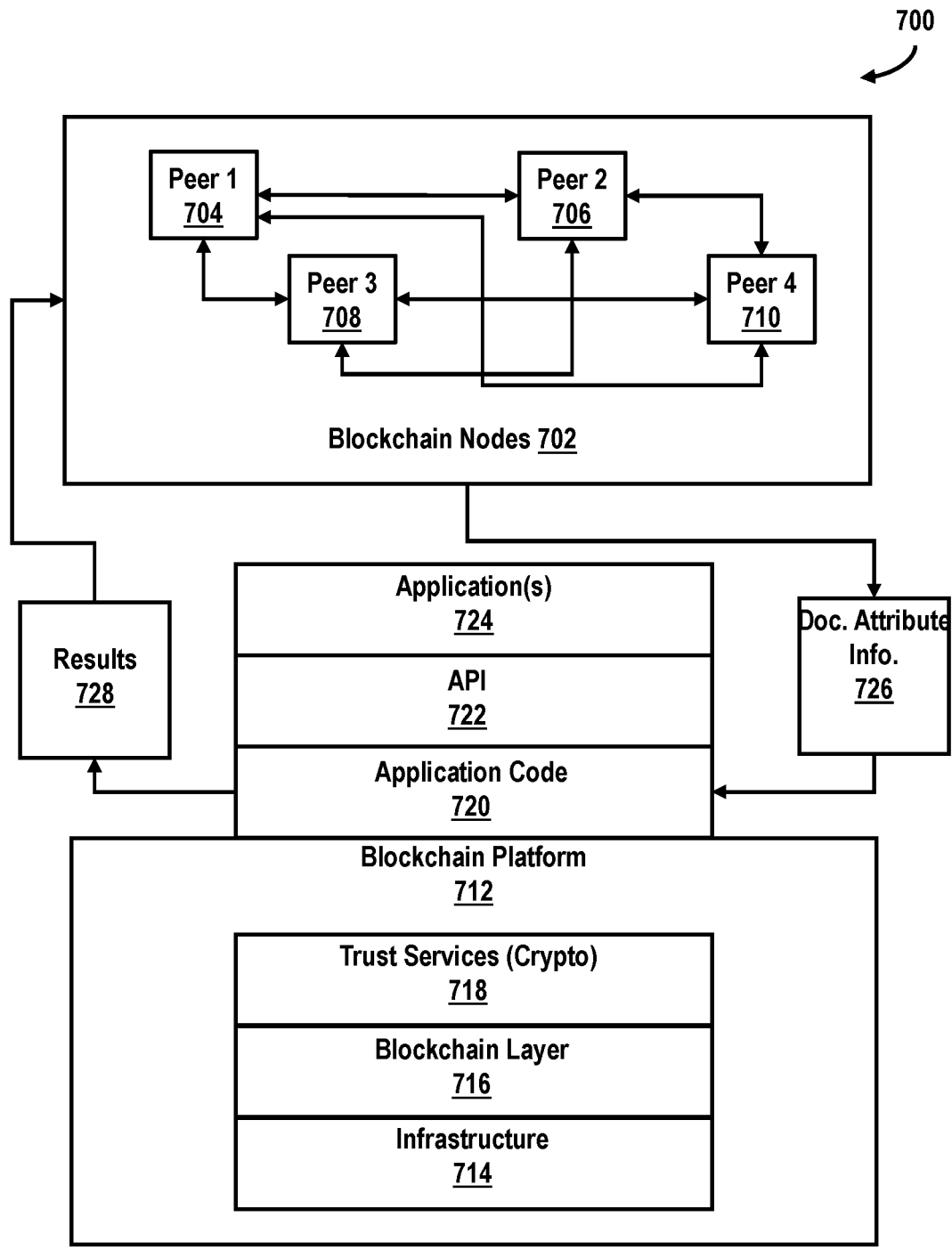
FIG. 7A depicts an example blockchain architecture configuration, consistent with some embodiments.

FIG. 7A illustrates a blockchain architecture configuration 700, consistent with some embodiments. The blockchain architecture 700 in these embodiments may include certain blockchain elements, for example, a group of blockchain nodes 702. The group of blockchain nodes 702, in turn, may include one or more member nodes 704-710 (these four nodes are depicted by example only). These member nodes 704-710 may participate in a number of activities, such as blockchain transaction addition and validation process (consensus). One or more of the member nodes 704-710 may endorse transactions based on endorsement policy and may provide an ordering service for all blockchain nodes in the architecture 700. A member node 704-710 may initiate a blockchain authentication and seek to write to a blockchain immutable ledger stored in blockchain layer 716, a copy of which may also be stored on the underpinning physical infrastructure 714.

The blockchain architecture 700 in some embodiments may include one or more applications 724, which are linked to application programming interfaces (APIs) 722 to access and execute stored program/application code 720 (e.g., chaincode, smart contracts, etc.). The stored program/application code 720, in turn, can be created according to a customized configuration sought by participants and can maintain its own state, control their own assets, and receive external information. The stored program/application code 720 can be deployed as a transaction and installed, via appending to the distributed ledger, on all blockchain nodes 704-710.

TABLE 7

| Blockchain ID | | | | Payload | | |
|---|---|---|---|---|---|---|
| id | user_id | tile_id | Lat_long | test_date | test_data | test_id |
| 666666 | bob@agrocompany.com | 007 | {−23.5808, −46.6409} | Jan. 1, 2019 | {pH: 6.5; Ca: 1000 mg/l; 100 Mg: mg/l; Al: 1 mg/l} | 12345 |
| 666667 | bob@agrocompany.com | 108 | {−22.9504, −43.1769} | Dec. 25, 2018 | {pH: 5.8; Ca: 900 mg/l; 120 Mg: mg/l; Al: 2 mg/} | 22334 |
| 666668 | bob@agrocompany.com | 209 | {−22.8999, −47.2012} | Apr. 1, 2018 | {pH: 4.3; Ca: 800 mg/l; 150 Mg: mg/l; Al: 3 mg/} | 98765 |
| ... | ... | ... | ... | ... | ... | ... |

In Table 7, each blockchain transaction record or block in the illustrative example may be associated with an entry in A blockchain base or platform 712 may include various layers of blockchain data, services (e.g., cryptographic trust services, virtual execution environment, etc.), and underpinning physical computer infrastructure that may be used to receive and store new transactions and provide access to auditors which are seeking to access data entries. A blockchain layer 716 may expose an interface that provides access to the virtual execution environment necessary to process the program code and engage a physical infrastructure 714. Cryptographic trust services 718 may be used to verify transactions such as asset exchange transactions and keep information private.

The blockchain architecture configuration of FIG. 7A may process and execute the program/application code 720 via one or more interfaces exposed, and services provided, by the blockchain platform 712. The program/application code 720 may control blockchain assets. For example, the code 720 can store and transfer data, and may be executed by member nodes 704-710 in the form of a smart contract and associated chaincode with conditions or other code elements subject to its execution. As a non-limiting example, smart contracts may be created to execute reminders, updates, and/or other notifications subject to the changes, updates, etc. The smart contracts can themselves be used to identify rules associated with authorization and access requirements and usage of the ledger. For example, document attribute(s) information 726 may be processed by one or more processing entities (e.g., virtual machines) included in the blockchain layer 716. A result 728 may include a plurality of linked shared documents. The physical infrastructure 714 may be utilized to retrieve any of the data or information described herein.

In some embodiments, the smart contract may be created via a high-level application and programming language, and then written to a block in the blockchain. The smart contract may include executable code that is registered, stored, and/or replicated with a blockchain (e.g., distributed network of blockchain peers). A transaction is an execution of the smart contract code that can be performed in response to conditions associated with the smart contract being satisfied. The executing of the smart contract may trigger a trusted modification(s) to a state of a digital blockchain ledger. The modification(s) to the blockchain ledger caused by the smart contract execution may be automatically replicated throughout the distributed network of blockchain peers through one or more consensus protocols in some embodiments.

The smart contract may write data to the blockchain in the format of key-value pairs. In some embodiments, the smart contract code can also read the values stored in a blockchain and use them in application operations. The smart contract code in these embodiments can then write the output of various logic operations into the blockchain. The smart contract code, in some embodiments, may be used to create a temporary data structure in a virtual machine or other computing platforms. Data written to the blockchain in these embodiments may be public or may be encrypted and maintained as private. The temporary data that is used/generated by the smart contract may be held in memory by the supplied execution environment, and then may be deleted once the data needed for the blockchain is identified.

The chaincode in some embodiments may comprise a code interpretation of a smart contract, with additional features. In some embodiments, the chaincode may be implemented as program code deployed on a computing network, where it is executed and validated by chain validators together during a consensus process. The chaincode may receive a hash and may retrieve from the blockchain a hash associated with the data template created by the use of a previously stored feature extractor. If the hashes of the hash identifier and the hash created from the stored identifier template data match, then the chaincode may send an authorization key to the requested service. The chaincode may write to the blockchain data associated with the cryptographic details.

Figure 7B:
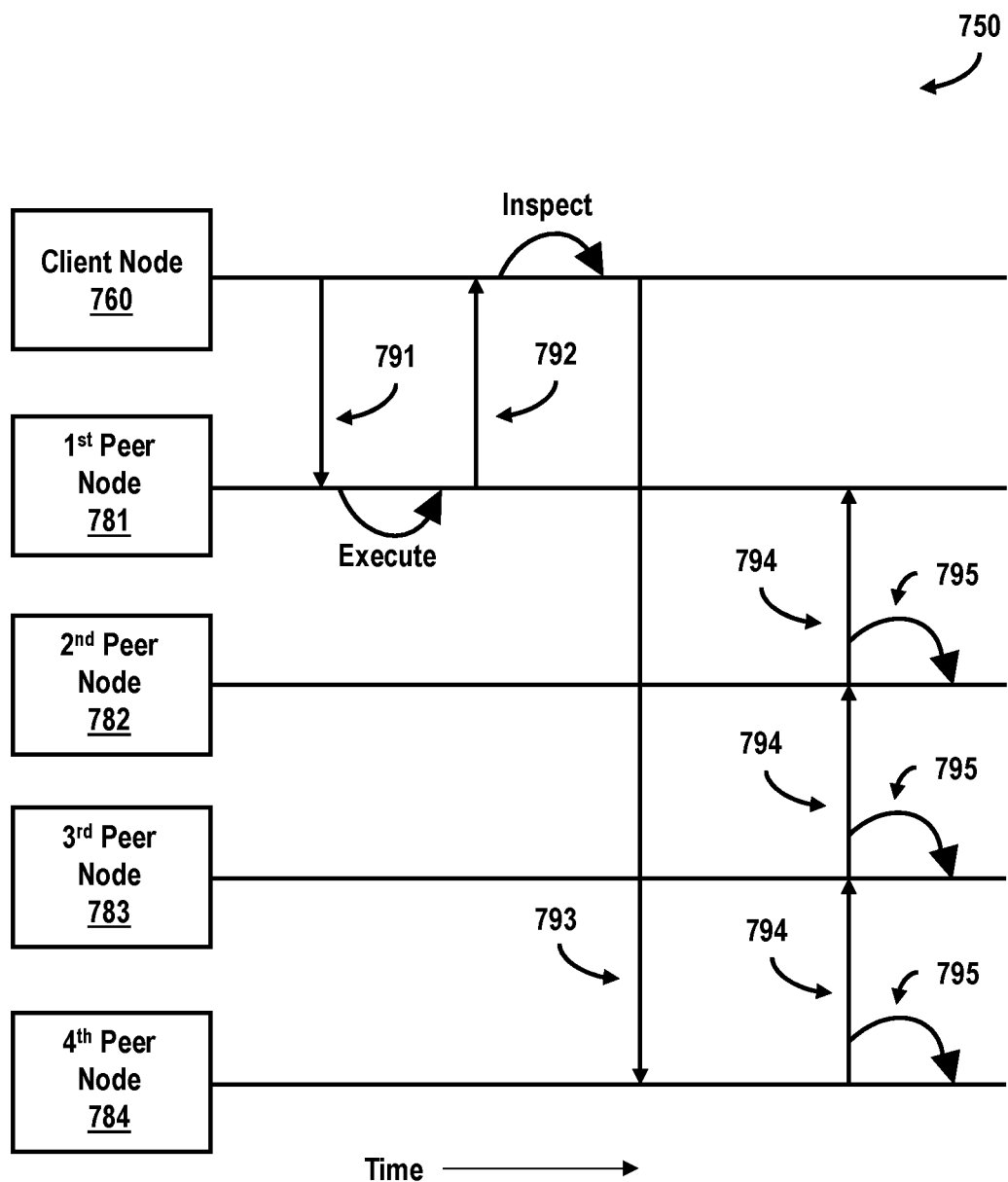
FIG. 7B illustrates a blockchain transactional flow, consistent with some embodiments.

FIG. 7B illustrates an example of a blockchain transactional flow 750 between nodes of the blockchain in accordance with some embodiments. The transaction flow in these embodiments may include a transaction proposal 791 sent by an application client node 760 to an endorsing peer node 781. The endorsing peer 781 may verify the client signature and execute a chaincode function to initiate the transaction. The output may include the chaincode results, a set of key/value versions that were read in the chaincode (read set), and the set of keys/values that were written in chaincode (write set). The proposal response 792 may then be sent back to the client 760, along with an endorsement signature, if approved.

In response, the client 760 may assemble the endorsements into a transaction payload 793 and broadcasts it to an ordering service node 784. The ordering service node 784 may then deliver ordered transactions as blocks to all peers 781-783 on a channel. Before committal to the blockchain, each peer 781-783 may validate the transaction. For example, the peers in some embodiments may check the endorsement policy to ensure that the correct allotment of the specified peers have signed the results and authenticated the signatures against the transaction payload 793.

With continuing reference to FIG. 7B, the client node 760 in some embodiments may initiate the transaction 791 by constructing and sending a request to the peer node 781, which may act an endorser. The client 760 may include an application leveraging a supported software development kit (SDK), which may utilize an available API to generate a transaction proposal. The transaction proposal, in turn, may be a request to invoke a chaincode function so that data can be read and/or written to the distributed ledger (i.e., write new key value pairs for the assets). The SDK may serve as a shim to package the transaction proposal into a properly architected format (e.g., protocol buffer over a remote procedure call (RPC)) and take the client's cryptographic credentials to produce a unique signature for the transaction proposal.

In response, the endorsing peer node 781 may verify: (a) that the transaction proposal is well-formed; (b) the transaction has not been submitted already in the past (replay-attack protection); (c) the signature is valid; and (d) that the submitter (client 760, in this example embodiment) is properly authorized to perform the proposed operation on that channel. The endorsing peer node 781 may take the transaction proposal inputs as arguments to the invoked chaincode function. The chaincode may then be executed against a current state database to produce transaction results, including a response value, read set, and write set. In some embodiments, no updates are made to the ledger at this point. Instead, the set of values, along with the endorsing peer node's 781 signature, may be passed back as a proposal response 792 to the SDK of the client 760, which parses the payload for the application to consume.

In response, the application of the client 760 may inspect/verify the endorsing peers' signatures and may compare the proposal responses to determine if the proposal response is the same. If the chaincode only queried the ledger, the application may inspect the query response and would typically not submit the transaction to the ordering service 784. If the client application intends to submit the transaction to the ordering service 784 to update the ledger, the application may determine if the specified endorsement policy has been fulfilled before submitting (i.e., did all peer nodes necessary for the transaction endorse the transaction). Here, the client may include only one of multiple parties to the transaction. In this case, each client may have their own endorsing node, and each endorsing node will need to endorse the transaction. The architecture is such that even if an application selects not to inspect responses or otherwise forwards an unendorsed transaction, the endorsement policy will still be enforced by peers and upheld at the commit validation phase.

After a successful inspection, in operation 793, the client 760 may assemble endorsements into a transaction and may broadcast the transaction proposal and response within a transaction message to the ordering service 784. The transaction may contain the read/write sets, the endorsing peers' signatures, and a channel ID. The ordering service 784 does not need to inspect the entire content of a transaction in order to perform its operation; instead the ordering service 784 may simply receive transactions from all channels in the network, order them chronologically by channel, and create blocks of transactions per channel.

The blocks of the transaction may be delivered from the ordering service 784 to all peer nodes 781-783 on the channel. The transactions 794 within the block may be validated to ensure any endorsement policy is fulfilled and to ensure that there have been no changes to ledger state for read set variables since the read set was generated by the transaction execution. Transactions in the block may be tagged as being valid or invalid. Furthermore, in operation 795, each peer node 781-783 may append the block to the channel's chain, and for each valid transaction, the write sets are committed to the current state database. An event may be emitted to notify the client application that the transaction (invocation) has been immutably appended to the chain, as well as to notify whether the transaction was validated or invalidated.

Permissioned Blockchains

Figure 8A:
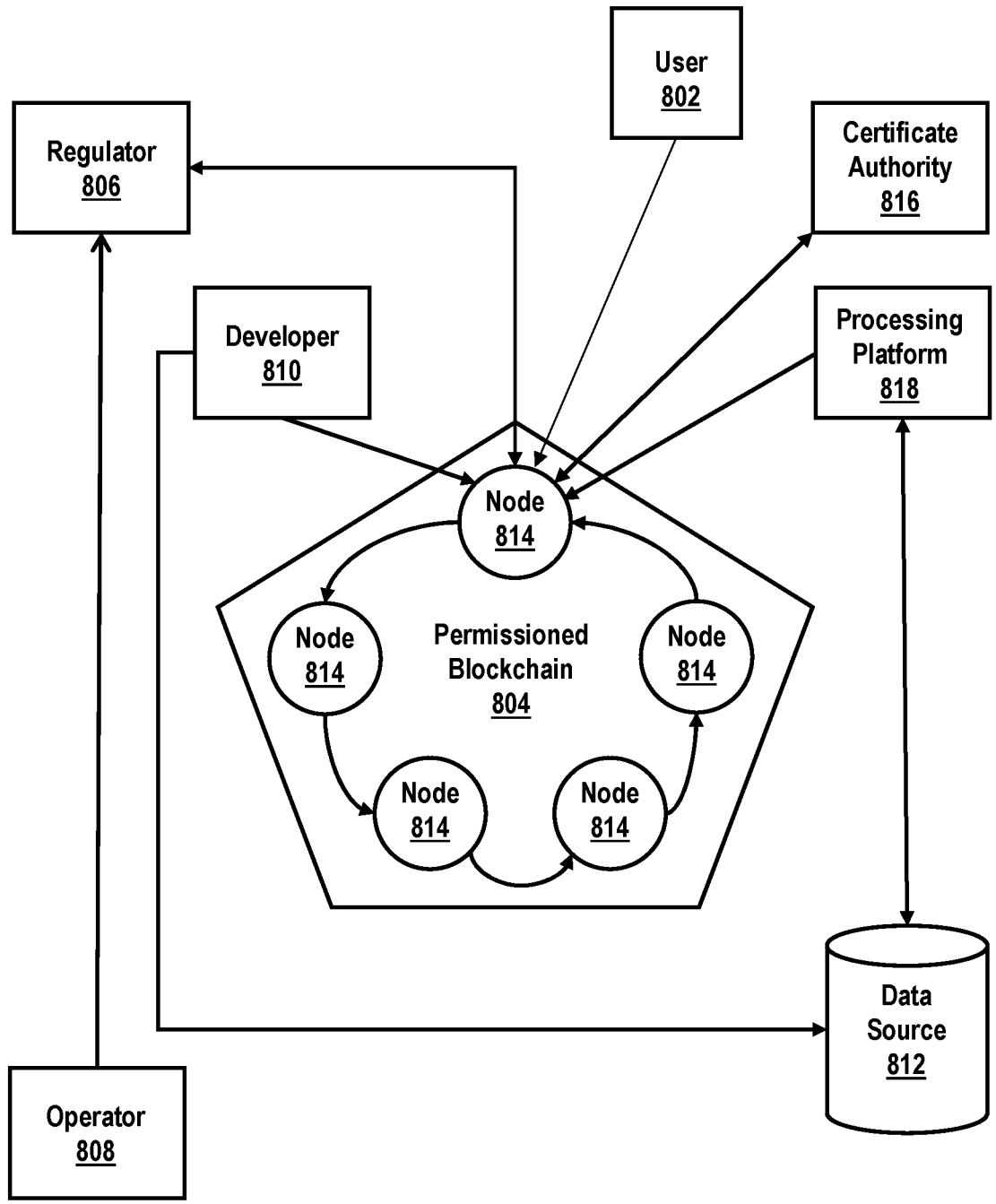
FIG. 8A illustrates a flow diagram, consistent with some embodiments.

FIG. 8A illustrates an example of a permissioned blockchain network, which features a distributed, decentralized peer-to-peer architecture, consistent with some embodiments. In this example, a blockchain user 802 may initiate a transaction to the permissioned blockchain 804. In this example, the transaction may be a deploy, invoke, or query, and may be issued through a client-side application leveraging an SDK, directly through an API, etc. Networks may provide access to a regulator 806, such as an auditor. A blockchain network operator 808 manages member permissions, such as enrolling the regulator 806 as an "auditor" and the blockchain user 802 as a "client." An auditor may be restricted only to querying the ledger, whereas a client may be authorized to deploy, invoke, and query certain types of chaincode.

A blockchain developer 810 can write chaincode and client-side applications in some embodiments. The blockchain developer 810 in these embodiments may deploy chaincode directly to the network through an interface. To include credentials from a traditional data source 812 in chaincode, the developer 810 may use an out-of-band connection to access the data. In this example, the blockchain user 802 may connect to the permissioned blockchain 804 through a peer node 814. Before proceeding with any transactions, the peer node 814 may retrieve the user's enrollment and transaction certificates from a certificate authority 816, which manages user roles and permissions. In some embodiments, blockchain users must possess these digital certificates in order to transact on the permissioned blockchain 804. In other embodiments, blockchain users may be authenticated using other techniques, such as via distributed chains of trust. Meanwhile, a user attempting to utilize chaincode may be required to verify their credentials on the traditional data source 812. Chaincode may use an out-of-band connection to this data through a traditional processing platform 818 to confirm the user's authorization.

Figure 8B:
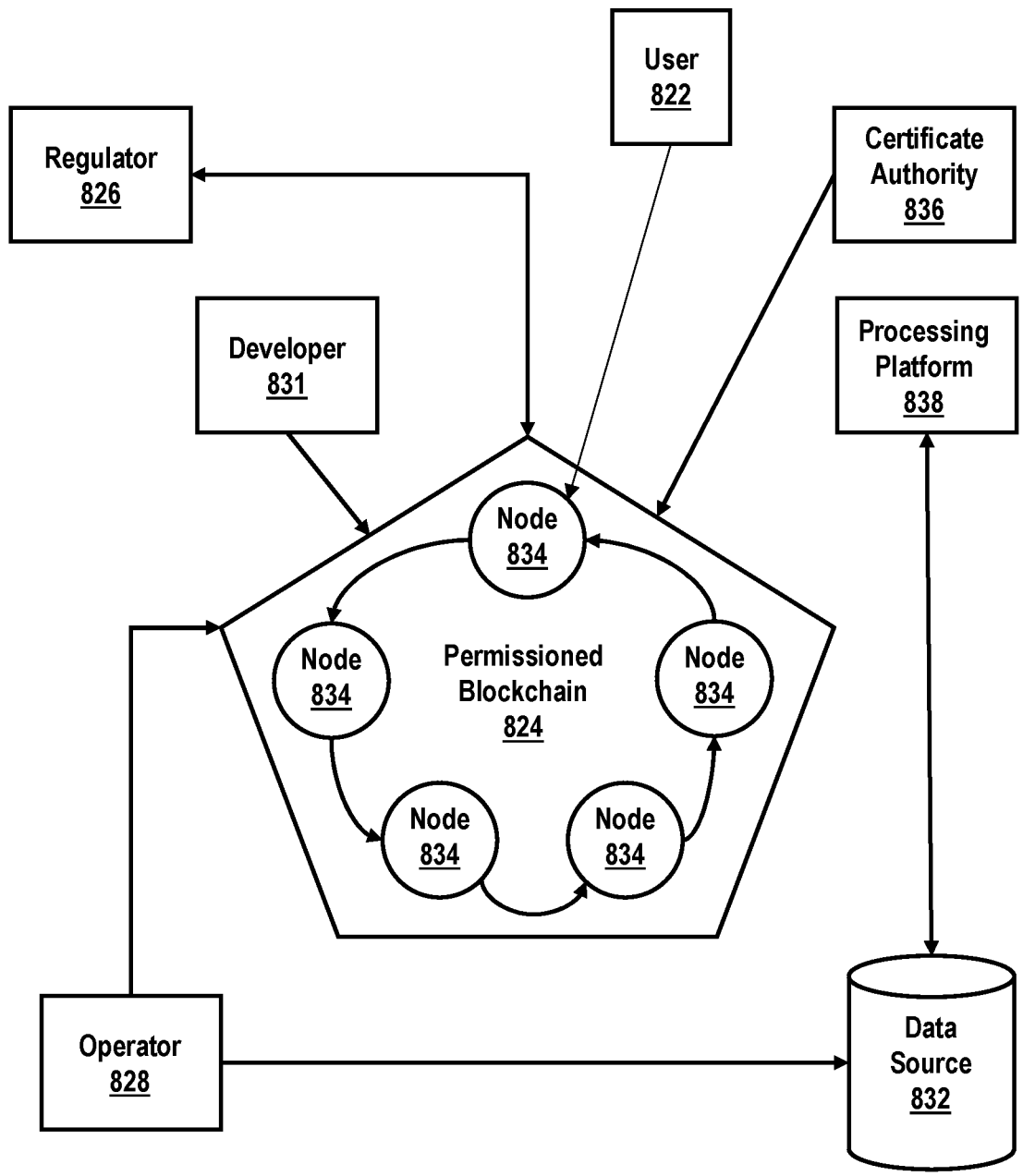
FIG. 8B illustrates a further flow diagram, consistent with some embodiments.

FIG. 8B illustrates another example of a permissioned blockchain network, which features a distributed, decentralized peer-to-peer architecture, consistent with some embodiments. In this example, a blockchain user 822 may submit a transaction to the permissioned blockchain 824. In this example, the transaction can be a deploy, invoke, or query, and may be issued through a client-side application leveraging an SDK, directly through an API, etc. Networks may provide access to a regulator 826, such as an auditor. A blockchain network operator 828 manages member permissions, such as enrolling the regulator 826 as an "auditor" and the blockchain user 822 as a "client." An auditor could be restricted only to querying the ledger, whereas a client could be authorized to deploy, invoke, and query certain types of chaincode.

A blockchain developer 831 in these embodiments may write chaincode and client-side applications. The blockchain developer 831 may deploy chaincode directly to the network through an interface. To include credentials from a traditional data source 832 in chaincode, the developer 831 may use an out-of-band connection to access the data. In this example, the blockchain user 822 connects to the network through a peer node 834. Before proceeding with any transactions, the peer node 834 retrieves the user's enrollment and transaction certificates from the certificate authority 836. In some embodiments, blockchain users must possess these digital certificates in order to transact on the permissioned blockchain 824. In other embodiments, blockchain users may be authenticated using other techniques, such as via distributed chains of trust. Meanwhile, a user attempting to utilize chaincode may be required to verify their credentials on the traditional data source 832. Chaincode can use an out-of-band connection to this data through a traditional processing platform 838 to confirm the user's authorization.

Figure 8C:
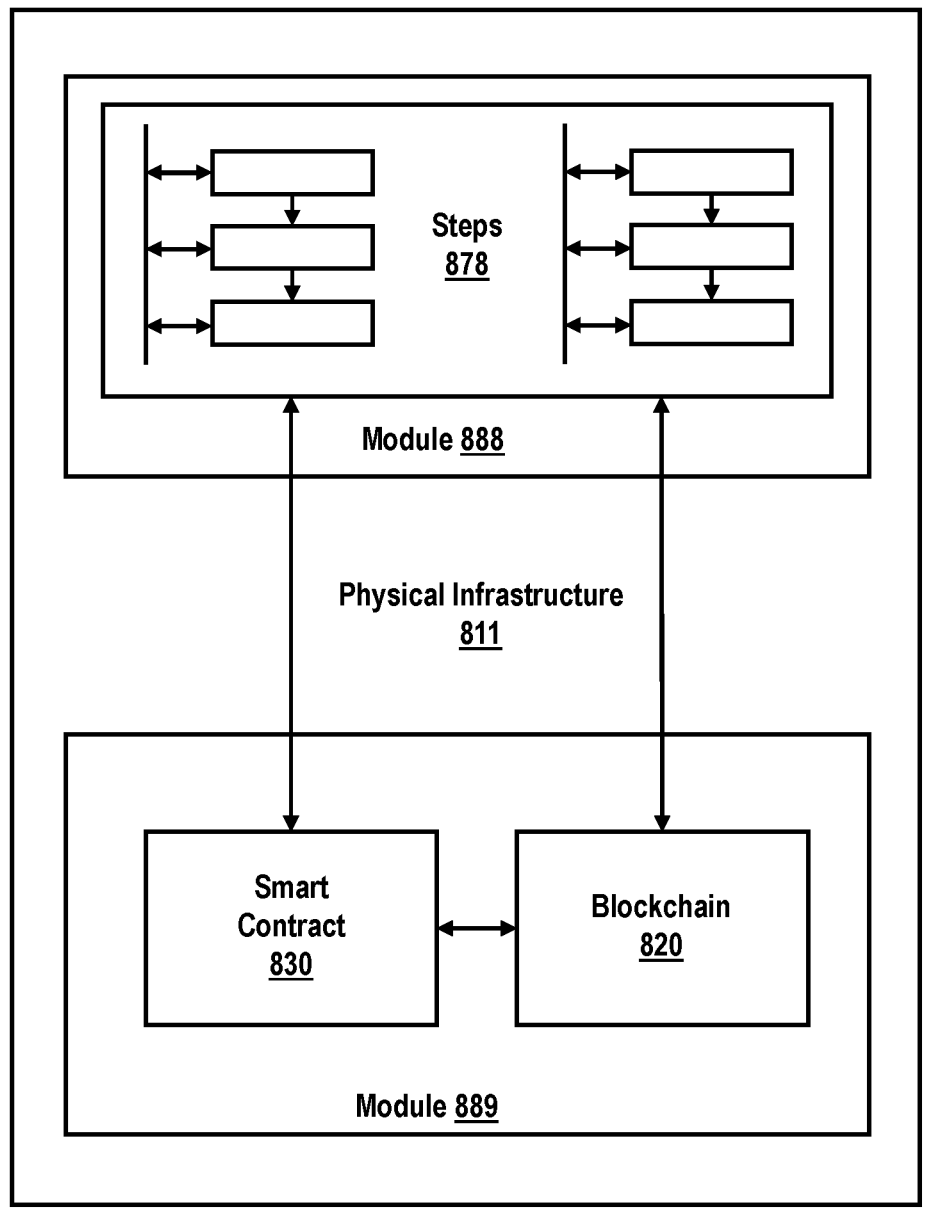
FIG. 8C illustrates an example system configured to perform one or more operations described herein, consistent with some embodiments.

FIG. 8C illustrates an example system that includes a physical infrastructure 811 configured to perform various operations, consistent with some embodiments. Referring to FIG. 8C, the physical infrastructure 811 includes a module 888 and a module 889. The module 819 includes a blockchain 820 and a smart contract 830 (which may reside on the blockchain 820) that may execute any of the operational steps 878 (in module 812) included in any of the example embodiments. The steps/operations 878 may include one or more of the embodiments described or depicted and may represent output or written information that is written or read from one or more smart contracts 830 and/or blockchains 820. The physical infrastructure 811, the module 888, and the module 889 may include one or more computers, servers, processors, memories, and/or wireless communication devices. Further, the module 888 and the module 889 may be the same module.

Figure 8D:
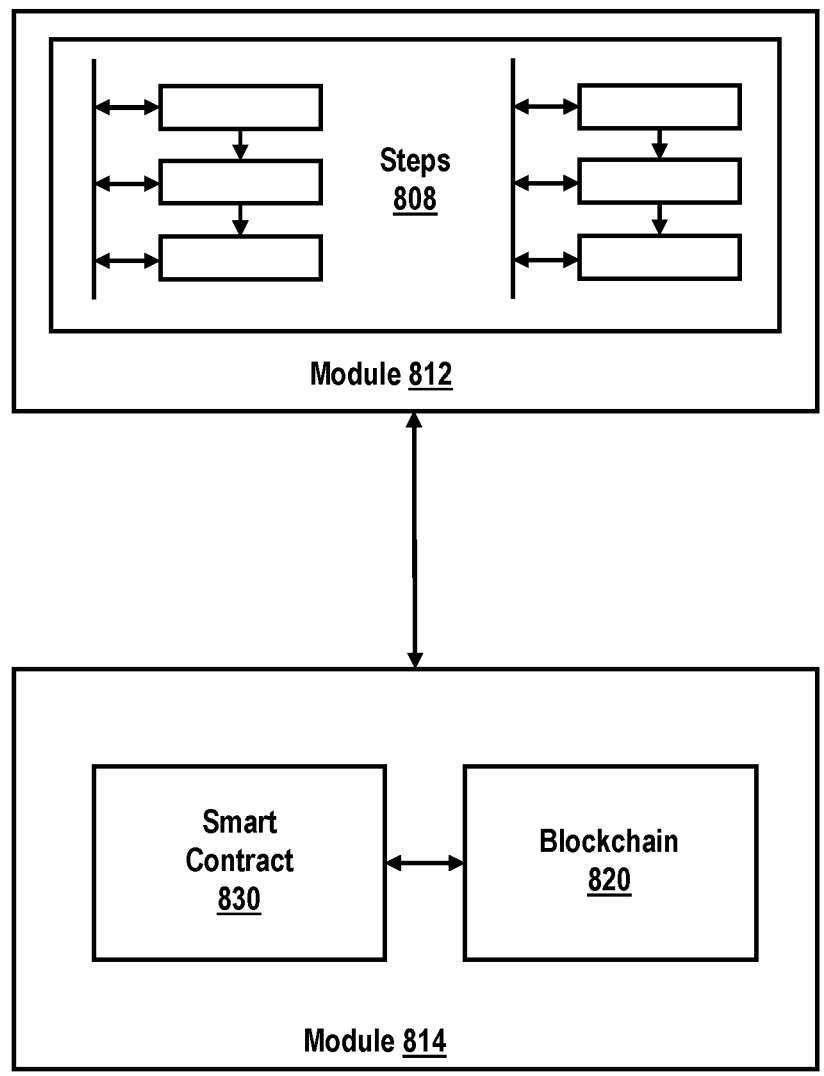
FIG. 8D illustrates another example system configured to perform one or more operations described herein, consistent with some embodiments.

FIG. 8D illustrates another example system configured to perform various operations, consistent with some embodiments. Referring to FIG. 8D, the system includes a module 812 and a module 814. The module 814 includes a blockchain 820 and a smart contract 830 (which may reside on the blockchain 820) that may execute any of the operational steps 878 (in module 812) included in any of the example embodiments. The steps/operations 878 may include one or more of the embodiments described or depicted and may represent output or written information that is written or read from one or more smart contracts 830 and/or blockchains 820. The physical module 812 and the module 814 may include one or more computers, servers, processors, memories, and/or wireless communication devices. Further, the module 812 and the module 814 may be the same module.

Figure 8E:
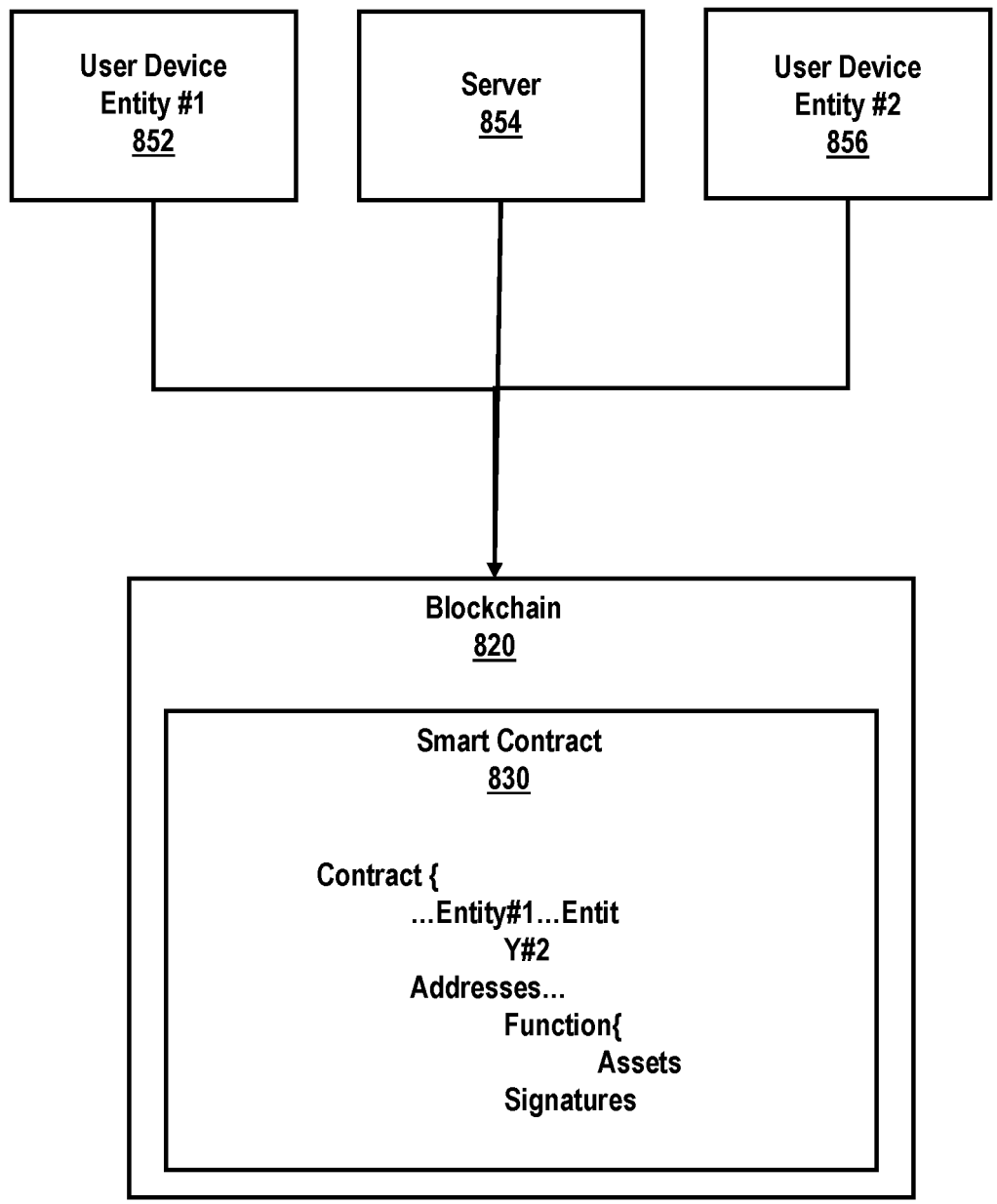
FIG. 8E illustrates a further example system configured to utilize a smart contract, consistent with some embodiments.

FIG. 8E illustrates an example system configured to utilize a smart contract configuration among contracting parties and a mediating server configured to enforce the smart contract terms on the blockchain 820, consistent with some embodiments. Referring to FIG. 8E, the configuration may represent a communication session, an asset transfer session, or a process or procedure that is driven by a smart contract 830, which explicitly identifies one or more user devices 852 and/or 856. The execution, operations, and results of the smart contract execution may be managed by a server 854. Content of the smart contract 830 may require digital signatures by one or more of the entities 852 and 856, which are parties to the smart contract transaction. The results of the smart contract execution may be written to a blockchain 820 as a blockchain transaction. The smart contract 830 resides on the blockchain 820, which may reside on one or more computers, servers, processors, memories, and/or wireless communication devices.

Figure 8F:
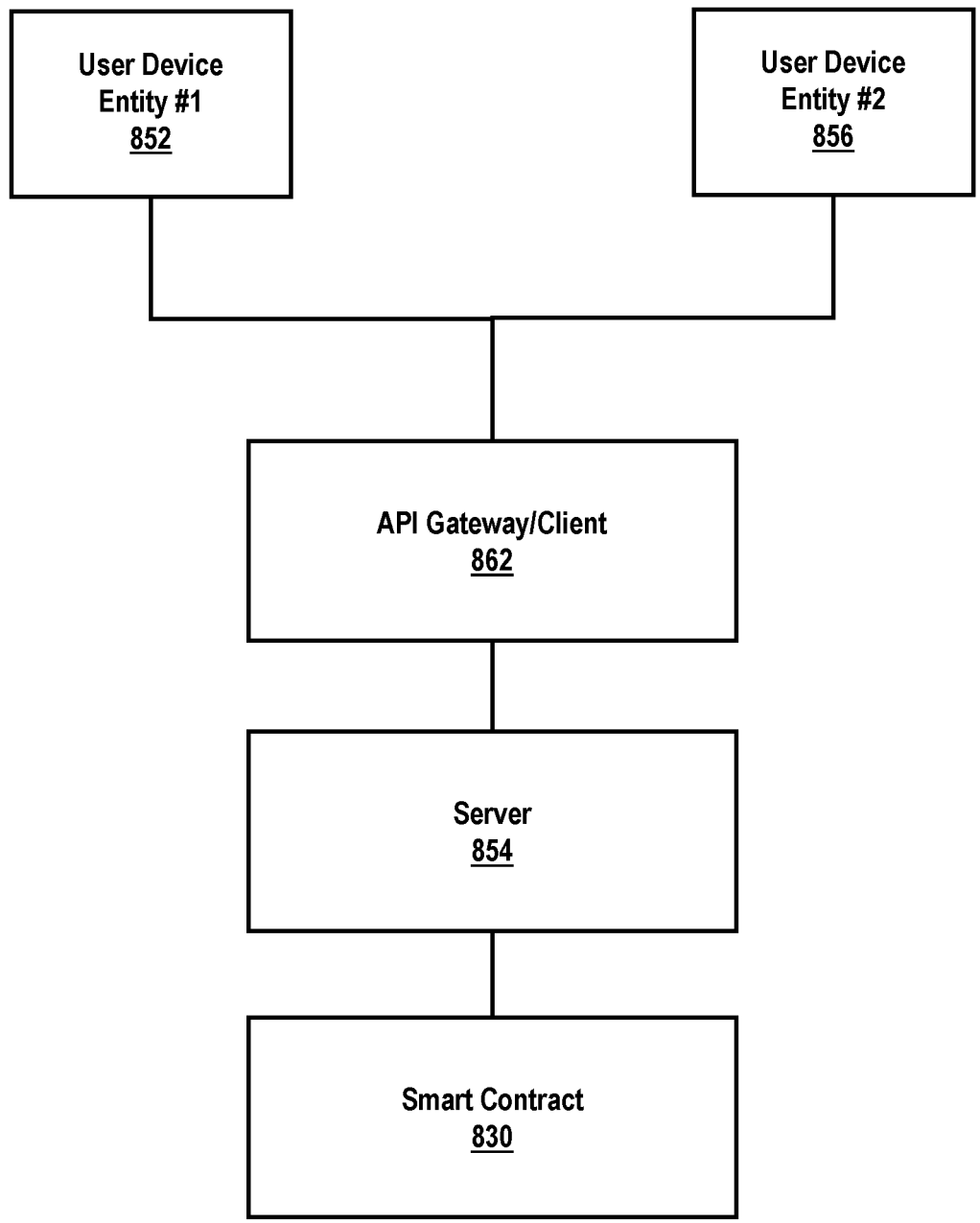
FIG. 8F illustrates a system including a blockchain, consistent with some embodiments.

FIG. 8F illustrates a system 860, including a blockchain, consistent with some embodiments. Referring to the example of FIG. 8D, an application programming interface (API) gateway 862 provides a common interface for accessing blockchain logic (e.g., smart contract 830 or other chaincode) and data (e.g., distributed ledger, etc.). In this example, the API gateway 862 is a common interface for performing transactions (invoke, queries, etc.) on the blockchain by connecting one or more entities 852 and 856 to a blockchain peer (i.e., server 854). Here, the server 854 is a blockchain network peer component that holds a copy of the world state and a distributed ledger allowing clients 852 and 856 to query data on the world stage as well as submit transactions into the blockchain network where depending on the smart contract 830 and endorsement policy, endorsing peers will run the smart contracts 830.

Block Processing

Figure 9A:
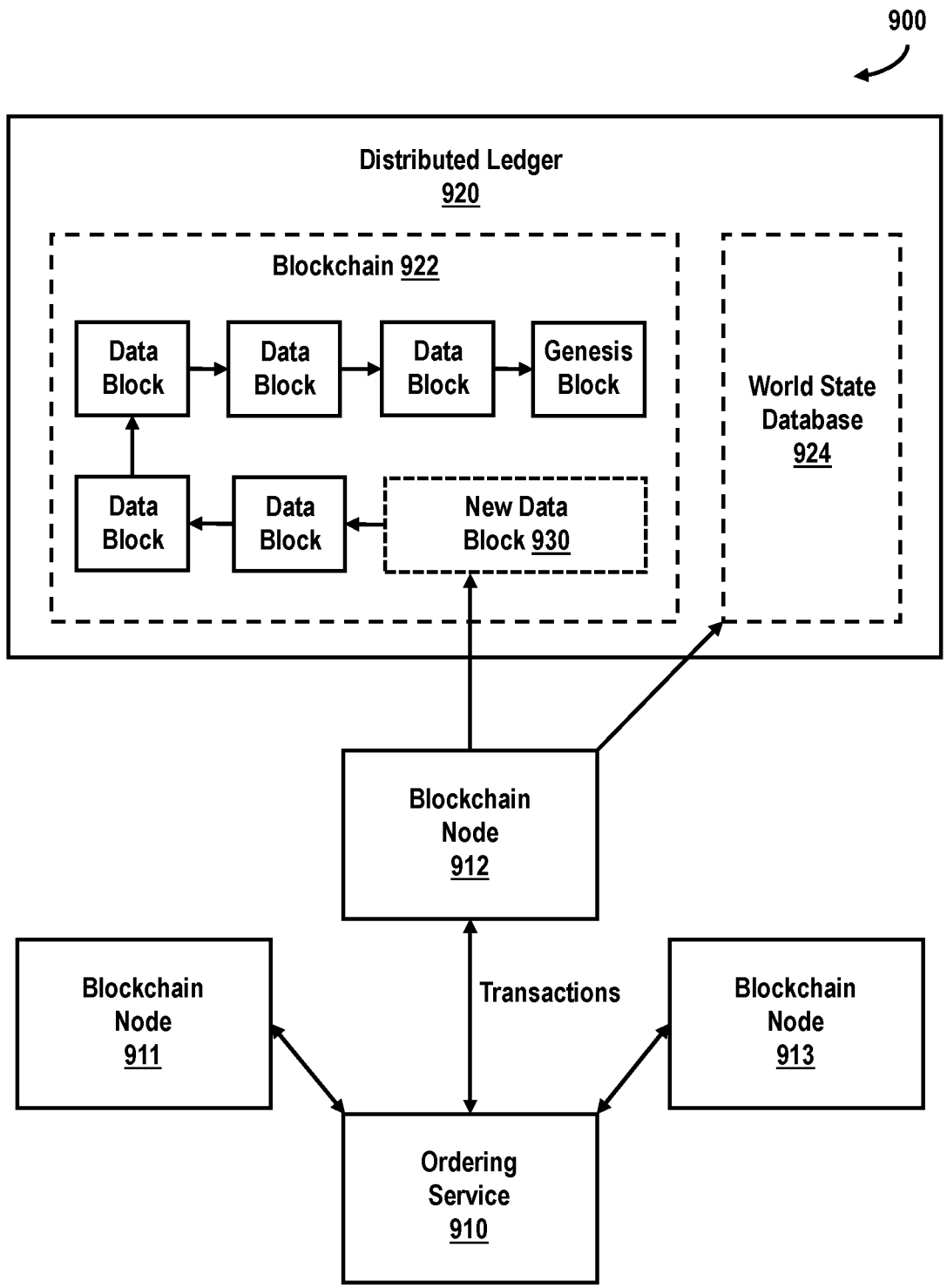
FIG. 9A illustrates a process for a new block being added to a distributed ledger, according to example embodiments.

FIG. 9A illustrates a process 900 of a new data block 930 being added to a distributed ledger 920, consistent with some embodiments, and FIG. 7B illustrates contents of a new data block 930 for blockchain, consistent with some embodiments. The new data block 930 may contain document linking data.

Referring to FIG. 9A, clients (not shown) may submit transactions to blockchain nodes 911, 912, and/or 913. Clients may be instructions received from any source to enact activity on the blockchain 922. As an example, clients may be applications that act on behalf of a requester, such as a device, person, or entity to propose transactions for the blockchain. The plurality of blockchain peers (e.g., blockchain nodes 911, 912, and 913) may maintain a state of the blockchain network and a copy of the distributed ledger 920. Different types of blockchain nodes/peers may be present in the blockchain network including endorsing peers which simulate and endorse transactions proposed by clients and committing peers which verify endorsements, validate transactions, and commit transactions to the distributed ledger 920. In some embodiments, the blockchain nodes 911, 912, and 913 may perform the role of endorser node, committer node, or both.

Figure 9B:
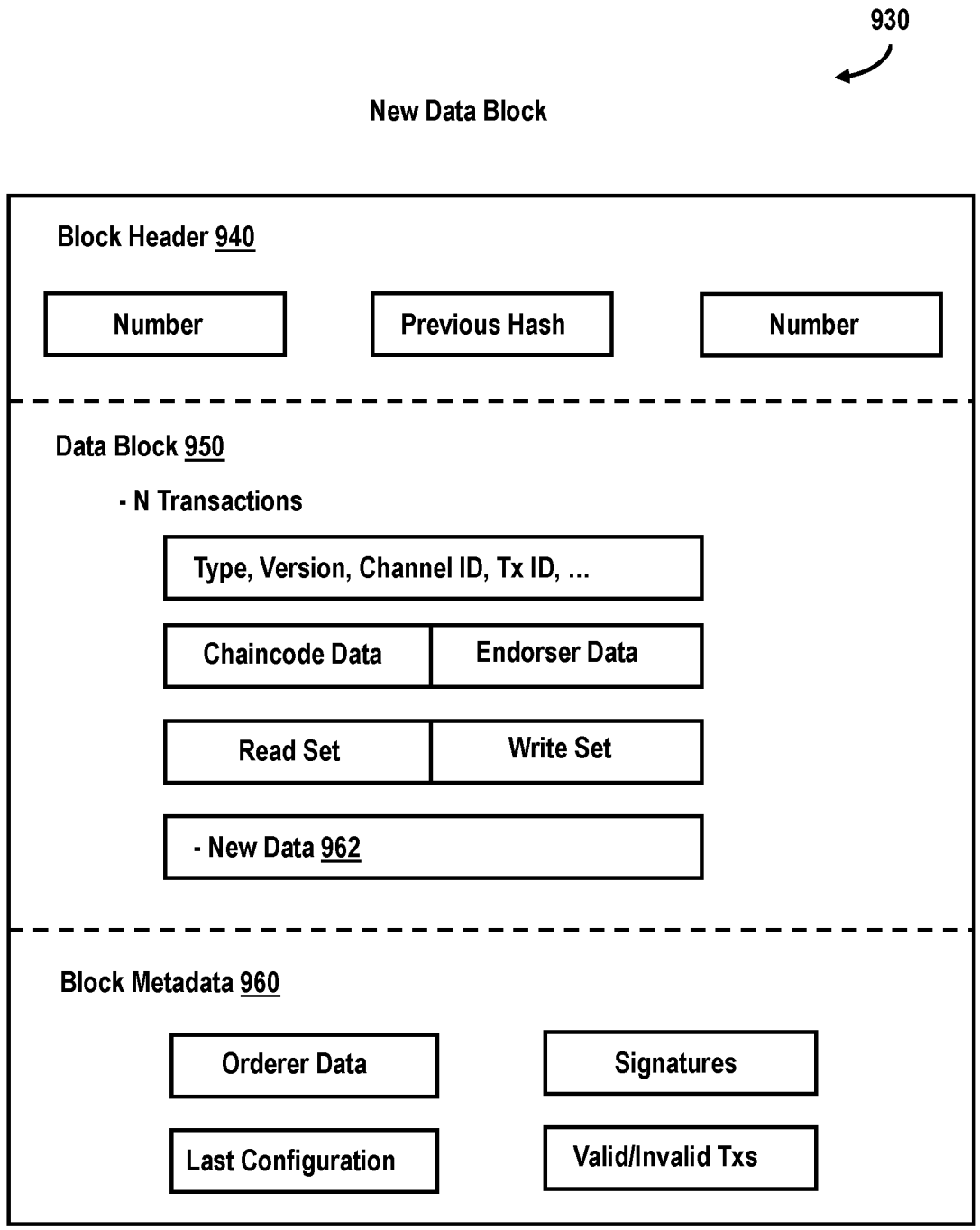
FIG. 9B illustrates contents of a new data block, according to example embodiments.

The distributed ledger 920 may include a blockchain which stores immutable, sequenced records in blocks, and a state database 924 (current world state) maintaining a current state of the blockchain 922. One distributed ledger 920 may exist per channel and each peer maintains its own copy of the distributed ledger 920 for each channel of which they are a member. The blockchain 922 may be a transaction log, structured as hash-linked blocks where each block contains a sequence of N transactions. Blocks may include various components such as shown in FIG. 9B. The linking of the blocks (shown by arrows in FIG. 9A) may be generated by adding a hash of a prior block's header within a block header of a current block. In this way, all transactions on the blockchain 922 may be sequenced and cryptographically linked together preventing tampering with blockchain data without breaking the hash links. Furthermore, because of the links, the latest block in the blockchain 922 represents every transaction that has come before it. The blockchain 922 may be stored on a peer file system (local or attached storage), which supports an append-only blockchain workload.

The current state of the blockchain 922 and the distributed ledger 920 may be stored in the state database 924. Here, the current state data represents the latest values for all keys ever included in the chain transaction log of the blockchain 922. Chaincode invocations execute transactions against the current state in the state database 924. To make these chaincode interactions more efficient, the latest values of all keys may be stored in the state database 924. The state database 924 may include an indexed view into the transaction log of the blockchain 922, it can therefore be regenerated from the chain at any time. The state database 924 may automatically get recovered (or generated if needed) upon peer startup, before transactions are accepted.

Endorsing nodes receive transactions from clients and endorse the transaction based on simulated results. Endorsing nodes hold smart contracts which simulate the transaction proposals. When an endorsing node endorses a transaction, the endorsing node creates a transaction endorsement, which is a signed response from the endorsing node to the client application indicating the endorsement of the simulated transaction. The method of endorsing a transaction depends on an endorsement policy that may be specified within chaincode. An example of an endorsement policy is "the majority of endorsing peers must endorse the transaction." Different channels may have different endorsement policies. Endorsed transactions are forward by the client application to ordering service 910.

The ordering service 910 accepts endorsed transactions, orders them into a block, and delivers the blocks to the committing peers. For example, the ordering service 910 may initiate a new block when a threshold of transactions has been reached, a timer times out, or another condition. In the example of FIG. 9A, blockchain node 912 is a committing peer that has received a new data new data block 930 for storage on blockchain 922. The first block in the blockchain may be referred to as a genesis block, which includes information about the blockchain, its members, the data stored therein, etc.

The ordering service 910 may be made up of a cluster of ordering nodes. The ordering service 910 in some embodiments may not process transactions, smart contracts, or maintain the shared ledger. Rather, the ordering service 910 in these embodiments may accept the endorsed transactions and specify the order in which those transactions are committed to the distributed ledger 920. The architecture of the blockchain network may be designed such that the specific implementation of "ordering" (e.g., Solo, Kafka, BFT, etc.) becomes a pluggable component.

Transactions in some embodiments may be written to the distributed ledger 920 in a consistent order. The order of transactions in these embodiments may be established to ensure that the updates to the state database 924 are valid when they are committed to the network. Unlike a cryptocurrency blockchain system (e.g., Bitcoin, etc.), where ordering occurs through the solving of a cryptographic puzzle, or mining, in this example the parties of the distributed ledger 920 may choose the ordering mechanism that best suits that network.

In some embodiments, when the ordering service 910 initializes a new data block 930, the new data block 930 may be broadcast to committing peers (e.g., blockchain nodes 911, 912, and 913). In response, each committing peer may validate the transaction within the new data block 930 by checking to make sure that the read set and the write set still match the current world state in the state database 924. Specifically, the committing peer may determine whether the read data that existed when the endorsers simulated the transaction is identical to the current world state in the state database 924. When the committing peer validates the transaction, the transaction may be written to the blockchain 922 on the distributed ledger 920, and the state database 924 may be updated with the write data from the read-write set. In some embodiments, if a transaction fails (e.g., if the committing peer finds that the read-write set does not match the current world state in the state database 924), the transaction ordered into a block may still be included in that block, but marked as invalid, and the state database 924 not updated.

Referring to FIG. 9B, a new data block 930 (also referred to as a data block) that is stored on the blockchain 922 of the distributed ledger 920 may include multiple data segments in some embodiments, such as a block header 940, block data 950, and block metadata 960. It should be appreciated that the various depicted blocks and their contents, such as new data block 930 and its contents, shown in FIG. 9B are merely examples and are not meant to limit the scope of the example embodiments. The new data block 930 may store transactional information of N transaction(s) (e.g., 1, 10, 100, 200, 1000, 2000, 3000, etc.) within the block data 950. The new data block 930 may also include a link to a previous block (e.g., on the blockchain 922 in FIG. 9A) within the block header 940. In particular, the block header 940 may include a hash of a previous block's header. The block header 940 may also include a unique block number, a hash of the block data 950 of the new data block 930, and the like. The block number of the new data block 930 may be unique and assigned in various orders, such as an incremental/sequential order starting from zero.

The block data 950 may store transactional information of each transaction that is recorded within the new data block 930. For example, the transaction data may include one or more of: a type of the transaction, a version, a timestamp, a channel ID of the distributed ledger 920, a transaction ID, an epoch, a payload visibility, a chaincode path (deploy tx), a chaincode name, a chaincode version, input (chaincode and functions), a client (creator) identify such as a public key and certificate, a signature of the client, identities of endorsers, endorser signatures, a proposal hash, chaincode events, response status, namespace, a read set (list of key and version read by the transaction, etc.), a write set (list of key and value, etc.), a start key, an end key, a list of keys, a Merkel tree query summary, and the like. The transaction data may be stored for each of the N transactions.

In some embodiments, the block data 950 may also store new data 962, which adds additional information to the hash-linked chain of blocks in the blockchain 922. The additional information may include one or more of the steps, features, processes and/or actions described or depicted herein. Accordingly, the new data 962 may be stored in an immutable log of blocks on the distributed ledger 920. Some of the benefits of storing such new data 962 are reflected in the various embodiments disclosed and depicted herein. Although in FIG. 9B the new data 962 is depicted in the block data 950, it could also be located in the block header 940 or the block metadata 960 in some embodiments. The new data 962 may also include a document composite key that is used for linking the documents within an organization.

The block metadata 960 may store multiple fields of metadata (e.g., as a byte array, etc.). Metadata fields may include: signature on block creation, a reference to a last configuration block, a transaction filter identifying valid and invalid transactions within the block, last offset persisted of an ordering service that ordered the block, and the like. The signature, the last configuration block, and the orderer metadata may be added by the ordering service 910. Meanwhile, a committer of the block (such as blockchain node 912) may add validity/invalidity information based on an endorsement policy, verification of read/write sets, and the like. The transaction filter may include a byte array of a size equal to the number of transactions in the block data 950 and a validation code identifying whether a transaction was valid/invalid.

Figure 9C:
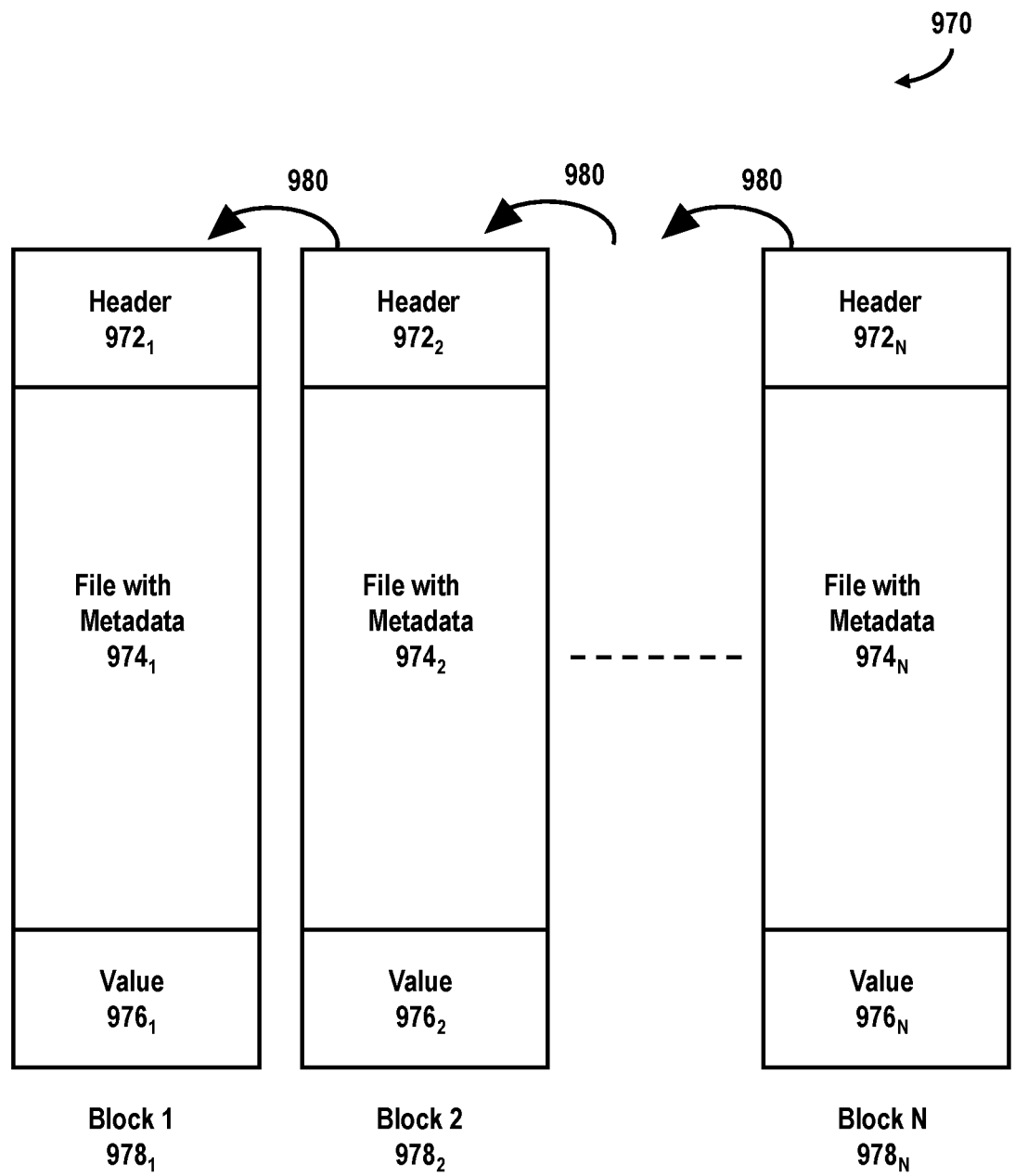
FIG. 9C illustrates a blockchain for digital content, according to example embodiments.

FIG. 9C illustrates an embodiment of a blockchain 970 for digital content, consistent with some embodiments. The digital content may include one or more files and associated information. The files may include transaction data, media, images, video, audio, text, links, graphics, animations, web pages, documents, or other forms of digital content. The immutable, append-only aspects of some blockchain embodiments may be desirable to serve as a safeguard to protect the integrity, validity, and authenticity of the digital content, making it suitable use in legal proceedings where admissibility rules apply or other settings where evidence is taken into consideration or where the presentation and use of digital information is otherwise of interest. In this case, the digital content may be referred to as digital evidence.

The blockchain in these embodiments may be formed in various ways. In one embodiment, the digital content may be included in and accessed from the blockchain itself. For example, each block of the blockchain may store a hash value of reference information (e.g., header, value, etc.) along the associated digital content. The hash value and associated digital content may then be encrypted together. Thus, the digital content of each block may be accessed by decrypting each block in the blockchain, and the hash value of each block may be used as a basis to reference a previous block. This may be illustrated as follows:

TABLE 8

| Block 1 | Block 2 | ... | Block N |
|---|---|---|---|
| Hash Value 1 | Hash Value 2 | | Hash Value N |
| Digital Content 1 | Digital Content 2 | | Digital Content N |

In one embodiment, the digital content may not be included in the blockchain. For example, the blockchain may store the encrypted hashes of the content of each block without any of the digital content. The digital content may be stored in another storage area or memory address in association with the hash value of the original file. The other storage area may be the same storage device used to store the blockchain or may be a different storage area or even a separate relational database. The digital content of each block may be referenced or accessed by obtaining or querying the hash value of a block of interest and then looking up that has value in the storage area, which is stored in correspondence with the actual digital content. This operation may be performed, for example, a database gatekeeper. This may be illustrated as follows:

TABLE 9

| Blockchain | Storage Area |
|---|---|
| Block 1 Hash Value | Block 1 Hash Value . . . Content |
| . | . |
| . | . |
| . | . |
| Block N Hash Value | Block N Hash Value . . . Content |

In the example embodiment of FIG. 7C, the blockchain 970 includes a number of blocks 978$_1$, 978$_2$, . . . 978$_N$ cryptographically linked in an ordered sequence, where N≥1. The encryption used to link the blocks 978$_1$, 978$_2$, . . . 978$_N$ may be any of a number of keyed or unkeyed Hash functions. In one embodiment, the blocks 978$_1$, 978$_2$, . . . 978$_N$ are subject to a hash function that produces n-bit alphanumeric outputs (where n is 256 or another number) from inputs that are based on information in the blocks. Examples of such a hash function include, but are not limited to: an SHA-type (SHA stands for Secured Hash Algorithm) algorithm, Merkle-Damgard algorithm, HAIFA algorithm, Merkle-tree algorithm, nonce-based algorithm, and a non-collision-resistant PRF algorithm. In another embodiment, the blocks 978$_1$, 978$_2$, . . . , 978$_N$ may be cryptographically linked by a function that is different from a hash function. For purposes of illustration, the following description is made with reference to a hash function, e.g., SHA-2.

Each of the blocks 978$_1$, 978$_2$, . . . , 978$_N$ in the blockchain may include a header, a version of the file, and a value. The header and the value may be different for each block as a result of hashing in the blockchain. In one embodiment, the value may be included in the header. As described in greater detail below, the version of the file may be the original file or may be a different version of the original file.

The first block 978$_1$ in the blockchain is referred to as the genesis block and may include the header 972$_1$, original file 974$_1$, and an initial value 976$_1$. The hashing scheme used for the genesis block, and indeed in all subsequent blocks, may vary. For example, all the information in the first block 978$_1$ may be hashed together and at one time, or each or a portion of the information in the first block 978$_1$ may be separately hashed, and then a hash of the separately hashed portions may be performed.

The header 972$_1$ may include one or more initial parameters, which, for example, may include a version number, timestamp, nonce, root information, difficulty level, consensus protocol, duration, media format, source, descriptive keywords, and/or other information associated with original file 974$_1$ and/or the blockchain. The header 972$_1$ may be generated automatically (e.g., by blockchain network managing software) or manually by a blockchain participant. Unlike the header in other blocks 978$_2$ to 978$_N$ in the blockchain, the header 972$_1$ in the genesis block may not reference a previous block, simply because there is no previous block.

The original file 974$_1$ in the genesis block may be, for example, data as captured by a device with or without processing prior to its inclusion in the blockchain. The original file 974$_1$ may be received through the interface of the system from the device, media source, or node. The original file 974$_1$ may be associated with metadata, which, for example, may be generated by a user, the device, and/or the system processor, either manually or automatically. The metadata may be included in the first block 978$_1$ in association with the original file 974$_1$.

The value 976$_1$ in the genesis block may be an initial value generated based on one or more unique attributes of the original file 974$_1$. In one embodiment, the one or more unique attributes may include the hash value for the original file 974$_1$, metadata for the original file 974$_1$, and other information associated with the file. In one implementation, the initial value 976$_1$ may be based on the following unique attributes:

1) SHA-2 computed hash value for the original file
2) originating device ID
3) starting timestamp for the original file
4) initial storage location of the original file
5) blockchain network member ID for software to currently control the original file and associated metadata The other blocks 978$_2$ to 978$_N$ in the blockchain also have headers, files, and values. However, unlike the header 972$_1$ of the first block, each of the headers 972$_2$ to 972$_N$ in the other blocks includes the hash value of an immediately preceding block. The hash value of the immediately preceding block may be just the hash of the header of the previous block or may be the hash value of the entire previous block. By including the hash value of a preceding block in each of the remaining blocks, a trace can be performed from the Nth block back to the genesis block (and the associated original file) on a block-by-block basis, as indicated by arrows 980, to establish an auditable and immutable chain-of-custody.

Each of the header 972$_2$ to 972$_N$ in the other blocks may also include other information, e.g., version number, timestamp, nonce, root information, difficulty level, consensus protocol, and/or other parameters or information associated with the corresponding files and/or the blockchain in general.

The files 974$_2$ to 974$_N$ in the other blocks may be equal to the original file or may be a modified version of the original file in the genesis block depending, for example, on the type of processing performed. The type of processing performed may vary from block to block. The processing may involve, for example, any modification of a file in a preceding block, such as redacting information or otherwise changing the content of, taking information away from, or adding or appending information to the files.

Additionally, or alternatively, the processing may involve merely copying the file from a preceding block, changing a storage location of the file, analyzing the file from one or more preceding blocks, moving the file from one storage or memory location to another, or performing action relative to the file of the blockchain and/or its associated metadata. Processing, which involves analyzing a file, may include, for example, appending, including, or otherwise associating various analytics, statistics, or other information associated with the file.

The values in each of the other blocks 976$_2$ to 976$_N$ in the other blocks are unique values and are all different as a result of the processing performed. For example, the value in any one block corresponds to an updated version of the value in the previous block. The update is reflected in the hash of the block to which the value is assigned. The values of the blocks, therefore, provide an indication of what processing was performed in the blocks and also permit a tracing through the blockchain back to the original file. This tracking confirms the chain-of-custody of the file throughout the entire blockchain.

For example, consider the case where portions of the file in a previous block are redacted, blocked out, or pixelated in order to protect the identity of a person shown in the file. In this case, the block, including the redacted file, will include metadata associated with the redacted file, e.g., how the redaction was performed, who performed the redaction, timestamps where the redaction(s) occurred, etc. The metadata may be hashed to form the value. Because the metadata for the block is different from the information that was hashed to form the value in the previous block, the values are different from one another and may be recovered when decrypted.

Figure 9D:
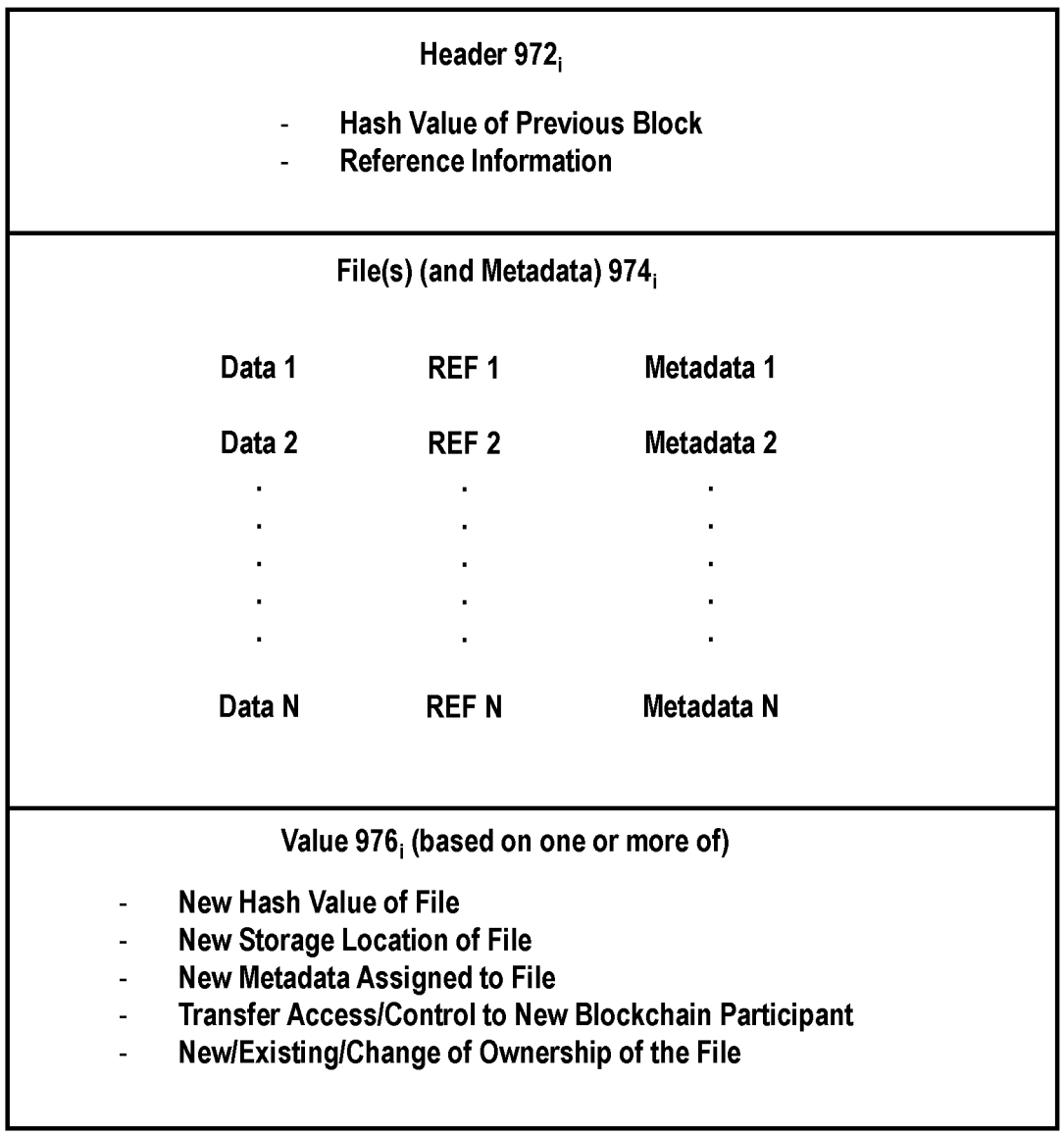
FIG. 9D illustrates a block which may represent the structure of blocks in the blockchain, according to example embodiments.

In one embodiment, the value of a previous block may be updated (e.g., a new hash value computed) to form the value of a current block when any one or more of the following occurs. The new hash value may be computed by hashing all or a portion of the information noted below, in this example embodiment.

a) new SHA-2 computed hash value if the file has been processed in any way (e.g., if the file was redacted, copied, altered, accessed, or some other action was taken)
b) new storage location for the file
c) new metadata identified associated with the file
d) transfer of access or control of the file from one blockchain participant to another blockchain participant FIG. 9D illustrates an embodiment of a block, which may represent the structure of the blocks in the blockchain 990, consistent with some embodiments. The block, $Block_i$, may include a header $972_i$, a file $974_i$, and a value $976_i$.

The header 972$i$ may include a hash value of a previous block $Block_{i-1}$, and additional reference information, which, for example, may be any of the types of information (e.g., header information including references, characteristics, parameters, etc.) discussed herein. All blocks in some embodiments may reference the hash of a previous block except the genesis block in some embodiments. The hash value of the previous block may be just a hash of the header in the previous block or a hash of all or a portion of the information in the previous block, including the file and metadata.

The file $974_i$ may include a plurality of data, such as Data 1, Data 2, . . . , Data N in sequence. The data are tagged with Metadata 1, Metadata 2, . . . , Metadata N, which describe the content and/or characteristics associated with the data. For example, the metadata for each data may include: information to indicate a timestamp for the data, process the data, keywords indicating the persons or other content depicted in the data, and/or other features that may be helpful to establish the validity and content of the file as a whole, and particularly its use a digital evidence, for example, as described in connection with an embodiment discussed below. In addition to the metadata, each data may be tagged with reference REF1, REF2, . . . , $REF_N$ to a previous data to prevent tampering, gaps in the file, and sequential reference through the file.

Once the metadata is assigned to the data (e.g., through a smart contract), the metadata cannot be altered without the hash changing in some embodiments, which can easily be identified for invalidation. The metadata in these embodiments, thus, creates a data log of information that may be accessed for use by participants in the blockchain.

The value $976_i$ in some embodiments may be a hash value or other value computed based on any of the types of information previously discussed. For example, for any given block $Block_i$, the value for that block may be updated to reflect the processing that was performed for that block, e.g., new hash value, new storage location, new metadata for the associated file, transfer of control or access, identifier, or other action or information to be added. Although the value in each block is shown to be separate from the metadata for the data of the file and header, the value may be based, in part or whole, on this metadata in another embodiment.

Once the blockchain 970 is formed, at any point in time, the immutable chain-of-custody for the file may be obtained by querying the blockchain for the transaction history of the values across the blocks in some embodiments. This query, or tracking procedure, may begin with decrypting the value of the block that is most currently included (e.g., the last (Nth) block), and then continuing to decrypt the value of the other blocks until the genesis block is reached and the original file is recovered. The decryption may involve decrypting the headers and files and associated metadata at each block, as well.

Decryption may be performed based on the type of encryption that took place in each block. This may involve the use of private keys, public keys, or a public key-private key pair. For example, when asymmetric encryption is used, blockchain participants or a processor in the network may generate a public key and private key pair using a predetermined algorithm. The public key and private key may be associated with each other through some mathematical relationship. The public key may be distributed publicly to serve as an address to receive messages from other users, e.g., an IP address or home address. The private key may be kept secret and may be used to digitally sign messages sent to other blockchain participants. The signature, in turn, may be included in the message so that the recipient can verify using the public key of the sender. This way, the recipient can be confident that only the sender could have sent this message.

In some embodiments, generating a key pair may be analogous to creating an account on the blockchain, but without having to actually register anywhere. In these embodiments, every transaction that is executed on the blockchain may be digitally signed by the sender using their private key. This signature may help ensure that only the owner of the account can track and process (if within the scope of permission determined by a smart contract) the file of the blockchain.

Computer Program Product

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

General

Any particular program nomenclature used in this description was merely for convenience, and thus the invention should not be limited to use solely in any specific application identified and/or implied by such nomenclature. Thus, for example, the routines executed to implement the embodiments of the invention, whether implemented as part of an operating system or a specific application, component, program, module, object, or sequence of instructions could have been referred to as a "program", "application", "server", or other meaningful nomenclature. Indeed, other alternative hardware and/or software environments may be used without departing from the scope of the invention.

Therefore, it is desired that the embodiments described herein be considered in all respects as illustrative, not restrictive, and that reference be made to the appended claims for determining the scope of the invention.

What is claimed is:

1. A validation method applied to sensor data prior to submitting to a blockchain, comprising:
providing a sensing device comprising a sensor element configured to perform a chemical measurement;

receiving, from the sensing device, a sensor captured result at an application, wherein the sensor captured result comprises a digitization of the chemical measurement;

obtaining a sample geolocation associated with the sensing device;

obtaining validation data based on the sample geolocation and domain-specific information;

applying the sensor captured result and the validation data to a domain-specific statistical model of expected range of variability of measured results to extract a distribution of expected sensor values;

computing a confidence value in the sensor captured result using the domain-specific statistical model;

validating the sensor captured result in response to determining that the confidence value is above a required threshold of confidence; and submitting the sensor captured result for appending to the blockchain in response to the validating.

2. The method of claim 1, further comprising:
submitting the sample geolocation to the blockchain.

3. The method of claim 1, the obtaining the validation data further comprising:
identifying, by the application, a non-overlapping tile identification (ID) for the sensor captured result; and
associating the sensor captured result with the non-overlapping tile ID.

4. The method of claim 3, further comprising retrieving, by the application, historical records for the non-overlapping tile from the blockchain.

5. The method of claim 4, further comprising:
identifying a plurality of neighboring non-overlapping tiles; and
retrieving, by the application, historical records for the plurality of neighboring non-overlapping tiles from the blockchain.

6. The method of claim 5, further comprising retrieving, by the application, geographical and domain specific data from a knowledge database.

7. The method of claim 6, wherein the geographical and domain specific data is chosen from the group consisting of current weather events, historical weather events, geographical knowledge, farming knowledge, and historical irrigation data.

8. The method of claim 6, wherein the domain-specific statistical model of expected range of variability comprises an artificial intelligence based model previously trained using data from a variety of geographical regions, the data comprising, per instance of non-overlapping tile, historical measurements and geolocation-sensitive domain-specific data extending on a plurality of non-overlapping geographical neighboring tiles, repeated over a plurality of tiles.

9. The method of claim 8, further comprising predicting an expected range for the sensor captured result using the artificial intelligence model, wherein the confidence value compares the sensor captured result to the expected range.

10. The method of claim 9, wherein the sensor captured result comprises a chemical test associated with an agricultural product to be delivered under a given food certification criteria.

11. The method of claim 1, further comprising:
receiving a universally unique identifier associated with the sensing device; and
validating the sensing device based on the universally unique identifier.

12. The method of claim 1, wherein the sensor captured result and the sample geolocation are appended to the blockchain only if the sensor captured result is validated.

13. The method of claim 1, further comprising:
receiving user information associated with the sensor captured result; and
appending the user information to the sensor captured result for submission to the blockchain.

14. The method of claim 1, further comprising updating a world state database with the sensor captured result.

15. The method of claim 1, wherein the validation method is performed at an intermediate credibility checking layer that validates the sensor captured data prior to appending the sensor captured data onto the blockchain.

16. The method of claim 15, wherein the intermediate credibility checking layer comprises a smart contract that automatically validates the confidence level against the required threshold of confidence.

17. The method of claim 16, wherein the smart contract automatically notifies one or more stakeholders that the confidence level is validated against the threshold of confidence.

18. A computer program product for validating sensor data prior to submitting to a blockchain, the computer program product comprising a computer readable storage medium having program instructions embodied therewith, the program instructions executable by a processor to cause the processor to:
receive a sensor captured result at an application, wherein the sensor captured result comprises a digitization of a chemical measurement performed by a sensor element of a sensing device;
receive a sample geolocation associated with the sensing device;
obtaining validation data based on the sample geolocation and domain-specific information;
apply the sensor captured result and the validation data to a domain-specific statistical model of expected range of variability of measured results to extract a distribution of expected sensor values;
compute a confidence value in the sensor captured result using the domain-specific statistical model;
validating the sensor captured result in response to determining that the confidence value is above a required threshold of confidence; and
submitting the sensor captured result for appending to the blockchain in response to the validating.

19. The computer program product of claim 18, wherein the validation method is performed at an intermediate credibility checking layer that validates the sensor captured result prior to appending the sensor captured data onto the blockchain.

20. A system for validating chemical data, comprising:
a cloud application adapted to:
receive a sensor captured result;
apply the sensor captured result to a domain-specific statistical model of expected range of variability of measured results to extract a distribution of expected sensor values;
calculate a distribution of expected sensor values, applying the sensor captured result;
compute a confidence value in the sensor captured result using the domain-specific statistical model;
validate the confidence value against a required threshold of confidence; and
append the sensor captured result to a blockchain;

a sensing device comprising a Universal Unique ID and a sensor element that generates the sensor captured result, wherein the sensing device is made of paper and performs chemical measurement of a sample using colorimetric reagents; and a mobile data processing system, wherein the mobile data processing system device is adapted to:
 digitize the sensor captured result;
 capture a geographic reference and a temporal reference associated with the sensor captured result; and
transmit the sensor captured result, the geographic reference, and the temporal reference to the cloud application.

* * * * *